US010732178B2

(12) United States Patent
Nimri et al.

(10) Patent No.: US 10,732,178 B2
(45) Date of Patent: Aug. 4, 2020

(54) DETECTION ASSAYS EMPLOYING MAGNETIC NANOPARTICLES

(71) Applicant: Bio-Rad HAIFA Ltd., Haifa (IL)

(72) Inventors: Shai Nimri, Kibbutz Nir David (IL); Vered Bronner, Adi (IL)

(73) Assignee: BIO-RAD HAIFA LTD., Haifa (IL)

( * ) Notice: Subject to any disclaimer, the term of this patent is extended or adjusted under 35 U.S.C. 154(b) by 26 days.

(21) Appl. No.: 14/167,428

(22) Filed: Jan. 29, 2014

(65) Prior Publication Data

US 2014/0212990 A1    Jul. 31, 2014

Related U.S. Application Data

(60) Provisional application No. 61/758,065, filed on Jan. 29, 2013.

(51) Int. Cl.
*G01N 33/543* (2006.01)
*G01N 33/53* (2006.01)

(52) U.S. Cl.
CPC . *G01N 33/54393* (2013.01); *G01N 33/54326* (2013.01); *G01N 33/54346* (2013.01)

(58) Field of Classification Search
None
See application file for complete search history.

(56) References Cited

U.S. PATENT DOCUMENTS

| | | | |
|---|---|---|---|
| 5,320,944 A | 6/1994 | Okada et al. | |
| 5,445,971 A * | 8/1995 | Rohr | G01N 33/54333 209/214 |
| 5,736,349 A | 4/1998 | Sasaki et al. | |
| 6,136,549 A * | 10/2000 | Feistel | G01N 33/54333 422/423 |
| RE37,891 E * | 10/2002 | Collins | B01L 3/502 435/15 |
| 7,314,763 B2 * | 1/2008 | Song | B01L 3/502761 435/969 |
| 7,927,561 B2 | 4/2011 | Kirakossian et al. | |
| 9,523,685 B2 * | 12/2016 | Charpentier | G01N 33/54333 |
| 9,562,896 B2 * | 2/2017 | Esch | C07K 1/22 |
| 2003/0049864 A1 | 3/2003 | Nakamura et al. | |
| 2003/0077598 A1 * | 4/2003 | Phan | C12Q 1/6834 435/6.11 |
| 2004/0067502 A1 * | 4/2004 | Guenther | C12Q 1/6816 435/6.11 |
| 2004/0115709 A1 * | 6/2004 | Morozov | G01N 33/561 435/6.12 |
| 2004/0209376 A1 * | 10/2004 | Natan | B01J 13/0047 436/56 |
| 2005/0032051 A1 | 2/2005 | Hayes et al. | |
| 2005/0142567 A1 * | 6/2005 | Su | G01N 21/6428 435/6.11 |
| 2009/0026079 A1 | 1/2009 | Margalit et al. | |
| 2009/0123939 A1 * | 5/2009 | Alocilja | G01N 27/745 435/7.2 |
| 2009/0203151 A1 * | 8/2009 | Matsuno | G01N 33/54346 436/518 |
| 2009/0325192 A1 * | 12/2009 | Kirakossian | B01L 3/508 435/7.2 |
| 2010/0044229 A1 | 2/2010 | Margalit et al. | |
| 2010/0233822 A1 * | 9/2010 | Prins | B01F 13/0809 436/164 |
| 2011/0275061 A1 * | 11/2011 | Weidemaier | G01N 21/658 435/6.1 |
| 2011/0294110 A1 * | 12/2011 | Blair | G01N 33/54346 435/5 |
| 2013/0171781 A1 | 7/2013 | Lee et al. | |
| 2014/0308756 A1 * | 10/2014 | Gautier | B22F 1/0018 436/501 |
| 2015/0355174 A1 * | 12/2015 | Blair | G01N 33/54333 435/7.93 |
| 2017/0146525 A1 * | 5/2017 | Luxton | G01N 33/54333 |

FOREIGN PATENT DOCUMENTS

| | | |
|---|---|---|
| CN | 102331492 | 1/2012 |
| EP | 0 339 980 B1 | 11/1989 |
| EP | 0 339 623 B1 | 12/1989 |
| WO | 2011/030286 A1 | 3/2011 |
| WO | 2011/045436 A1 | 4/2011 |
| WO | 2011/155890 A1 | 12/2011 |

OTHER PUBLICATIONS

Hong et al. J. Immunological Methods 2011 365:95-100.*
Urbach, et al., "Sub-100 nm Confinement of Magnetic Nanoparticles Using Localized Magnetic Field Gradients", J. Am Chem. Soc. vol. 125, pp. 12704-12705, (2003).
Osman, et al., "A Novel Device for Continuous Flow Magnetic Trapping and Sorting of Human Cells Using Flat Micro-Patterned NdFeB Films", 15th International Conference on Miniaturized Systems for Chemistry and Life Sciences, pp. 515-517, (2011).
Luxton et al., "Use of External Magnetic Fields To Reduce Reaction Times in an Immunoassay Using Micrometer-Sized Paramagnetic Particles as Labels (Magnetoimmunoassay)", Analytical Chemistry, vol. 76, No. 6. pp. 1715-1719, (2004).
Dittmer et al., "Sensitive and rapid immunoassay for parathyroid hormone using magnetic particle labels and magnetic actuation", vol. 338, pp. 40-46, (2008).
Bruls et al., "Rapid integrated biosensor for multiplexed immunoassays based on actuated magnetic nanoparticles", Lab Chip, vol. 9, pp. 3504-3510, (2009).
Lee et al., "Accelerated Immunoassays Based on Magnetic Particle Dynamics in a Rotating Capillary Tube with Stationary Magnetic Field", Analytical Chemistry, vol. 84, pp. 8317-8322, (2012).
Cheng et al., "Rapid and sensitive detection of rare cancer cells by the coupling of immunomagnetic nanoparticle separation with ELISA analysis", International Journal of Nanomedicine, vol. 7, pp. 2967-2973, (2012).

(Continued)

*Primary Examiner* — Changhwa J Cheu
(74) *Attorney, Agent, or Firm* — Browdy and Neimar, PLLC

(57) ABSTRACT

The present invention is directed to novel assays for detecting target molecules. The assays employ small size, detectably labeled, magnetic nanoparticles associated with a capture molecule. The detection assay is accelerated by applying magnetic field during the assay. The assays of the invention can be used to enhance the efficiency of the detection step in dot blot, Western blot and ELISA.

24 Claims, 16 Drawing Sheets

(56) References Cited

OTHER PUBLICATIONS

Lenglet et al., "Magnetic-bead detection technologies exploit the nonlinear features of superparamagnetic materials embedded in magnetic beads", Magnetic immunoassays: A new paradigm in POCT, IVD Technology (http://www.ivdtechnology.com), (2008).
Osterfeld et al., "Multiplex protein assays based on real-time magnetic nanotag sensing", PNAS, vol. 105, No. 52, pp. 20637-20640, (2008).
The International Search Report and Written Opinion for corresponding International Application No. PCT/IL2014/050101, dated May 11, 2014, ten pages; PCT/ISA/220, PCT/ISA/210, and PCT/ISA/237.
Hyo-Bong Hong et al., Detection of two different influenza A viruses using a nitrocellulose membrane and a magnetic biosensor, Journal of Immunological Methods, 365(1):95-100 (2011).
Kan Wang et al., BRCAA1 monoclonal antibody conjugated fluorescent magnetic nanoparticles for in vivo targeted magnetofluorescent imaging of gastric cancer, Journal of Nanobiotechnology, 9(1):23 (2011).

\* cited by examiner

MNPs (100 μg/ml in PBS):

hSA/hT: 50 – 25 – 12.5 – 6.2 – 3.1 – 1.6 – 0.8 – 0.4 – 0.2 ng

Figure 20A Wet membrane hSA

Figure 20B hT

Figure 20C Dried membrane hSA / hT : 20.0 - 6.7 - 2.2 - 0.74 - 0.25 - 0.082 - 0.027 - 0.009 ng

DETECTION ASSAYS EMPLOYING MAGNETIC NANOPARTICLES

TECHNOLOGICAL FIELD

The present invention relates to accelerated assays for detection of target molecules.

PRIOR ART

References considered to be relevant as background to the presently disclosed subject matter are listed below:
[1] WO2011/030286
[2] US 2005/0032051
[3] WO2011/045436
[4] EP 0339980
[5] WO 2011/155890
[6] U.S. Pat. No. 7,927,561
[7] U.S. Pat. No. 5,736,349
[8] U.S. Pat. No. 5,320,944
[9] US 2003/0049864
[10] EP 0339623
[11] Urbach, A. R. et al., *J. Am Chem. Soc.* 2003, 125, 12704-12705
[12] Osman, O. et al., 15*th International Conference on Miniaturized Systems for Chemistry and Life Sciences* Oct. 2-6, 2011, Seattle, Wash., USA Acknowledgement of the above references herein is not to be inferred as meaning that these are in any way relevant to the patentability of the presently disclosed subject matter.

BACKGROUND

Assays are commonly used for detecting target molecules in a sample for research or diagnostic purposes.

U.S. Pat. No. 7,927,561 discloses methods of detecting an analyte in a fluid sample. The fluid sample is incubated with magnetic particles coated with binding molecules directed to the analyte. The method is based on concentrating the magnetically labeled analyte to a detection region using a focusing magnet.

WO 2011/045436 discloses a lateral flow assay device and a method of detecting an analyte in a liquid sample. The lateral flow assay device comprises a sample zone and a reaction zone forming a flow path for the sample. The method employs a first capture molecule which carries a non-magnetic label and a second capture molecule which carries a magnetic particle.

WO 2011/030286 discloses a method for detection of an analyte in a sample comprising a plurality of capture moieties capable of binding to said analyte. At least one of the capture moieties is bound to a solid substrate and at least one other capture moiety is bound to a detectable marker, wherein the detectable marker is a large particle marker having a particle size of ≥50 nm-≤5,000 nm. This assay is performed as a "sandwich assay" in which the analyte is caught between two different capture molecules.

Many detection assays involve immobilization of target molecules onto a porous substrate (e.g. a membrane) followed by incubation with target binding agents (e.g. Dot blot or Western blot). The target binding agents are labeled (either directly or via a secondary binding agent) such that upon performing a suitable reaction, a signal is formed indicating the presence of the target molecule and its amount.

The Western blotting workflow is long, arduous and often takes more than a day from start to finish. After protein transfer to the blotting membrane there is a development process that takes from 3-4 hours to overnight to complete. The development process includes membrane blocking, antibody probing, repetitive membrane washing and signal detection; this is the most tedious portion of the entire workflow.

Therefore there is a need for developing an assay that improves the speed of substrate-based detection methods.

GENERAL DESCRIPTION

The present invention is based on the finding that the association of target binding agents (capture molecules) with magnetic nanoparticles (MNPs), preferably with magnetic nanoparticles having a small diameter, and applying magnetic field during the assay, largely enhanced the efficiency of the detection step in dot blot, Western blot and ELISA analysis assays.

The fact that using MNPs with a relatively small diameter had such an enhancing effect on the speed and efficiency of the detection assay was surprising. As demonstrated in the Examples below, reliable assay results were obtained within minutes.

Without wishing to be bound by theory, the exemplified advantages of using small MNPs over the prior art assays which employ larger MNPs may arise from the following reasons:

A. The small size of the MNP allows the infiltration of the particles into a substrate having small pores, thereby allowing binding to the target molecules which are immobilized within the substrate's pores. Therefore, magnetic acceleration of assays like Dot blot and Western blot may be possible only with small MNPs which are much smaller than the average pore size of the commonly used membranes in these assays.

B. Using larger MNPs might impose limitations on the assay's dynamic range. Use of a large MNP to detect smaller molecules (even macromolecules such as proteins) attached to a solid substrate may saturate the substrate with MNP and thereby interfere with the assay dynamics. Namely, one MNP will bind to more than one molecule even when a low amount of molecules is present on the substrate, and thus the higher limit of detection will be relatively low. In contrast, using small MNPs, e.g. with similar dimensions to the target macromolecules, will enable a 1:1 binding ratio even when a high amount of molecules is present on the substrate, and thus higher dynamic range will be gained.

C. The solubility of small MNPs is generally better than that of large MNPs, and results in a better assay performance, e.g. in terms of signal uniformity over the surface and lower background due to less sedimentation on the surface.

Therefore, in a first aspect, the present invention provides an assay for detecting a target molecule comprising:
  a. Incubating a substrate potentially comprising at least one target molecule with detectably labeled magnetic nanoparticle (MNP) complexes, wherein said MNP complexes comprise MNP having a small diameter associated with a capture molecule capable of binding directly or indirectly to said target molecule;
  b. Applying magnetic field; and
  c. Subjecting the incubated substrate to a detection step; whereby the presence of a detection signal is indicative of the presence of the target molecule and the signal intensity is indicative of the amount of the target molecule.

In a second aspect the present invention provides an assay for detecting a target molecule comprising:
a. Providing detectably labeled magnetic nanoparticle (MNP) complexes, wherein said MNP complexes comprise MNP associated with a secondary binding agent capable of binding a primary binding agent;
b. Incubating said MNP complexes with a primary binding agent, thereby forming a second MNP complex comprising MNP, a secondary binding agent, and a primary binding agent;
c. Incubating a substrate potentially comprising at least one target molecule with said second MNP complex;
d. Applying magnetic field; and
e. Subjecting the incubated sample to a detection reaction;
whereby the presence of a detection signal is indicative of the presence of the target molecule and the signal intensity is indicative of the amount of the target molecule.

In another aspect, the present invention provides an assay system comprising a substrate potentially comprising at least one target molecule; at least one detectably labeled MNP complex, wherein said MNP complex comprises MNP having a small diameter associated with a capture molecule capable of binding directly or indirectly to said target molecule; and at least one magnet.

In another aspect, the present invention provides a detectably labeled MNP complex comprising magnetic nanoparticles having a small diameter associated with a capture molecule capable of binding directly or indirectly to a target molecule, for use in an assay for the detection of said target molecule wherein said target molecule is immobilized onto a substrate.

In one embodiment said substrate is a porous substrate. The porous substrate may be a membrane, a filter or a gel.

In one embodiment, the average pore size of the porous substrate is larger than the average diameter of the MNPs.

In another embodiment said substrate is a non-porous substrate.

In one embodiment said capture molecule is a primary binding agent.

In another embodiment, said capture molecule is a secondary binding agent.

In one embodiment the substrate is incubated with a primary binding agent prior to the incubation with the MNP complex comprising said secondary binding agent.

In another embodiment, the MNP complex comprising said secondary binding agent is incubated with a primary binding agent prior to the incubation with the substrate.

In certain embodiments, said primary binding agent is a primary antibody.

In certain embodiment, the secondary binding agent is a secondary antibody.

In one embodiment the MNP in the MNP complex is detectably labeled.

In another embodiment, the capture molecule in the MNP complex is detectably labeled.

The labeling agent may be selected from the group consisting of a fluorescent compound, such as fluorescein (or a fluorescein derivative such as FITC) or phycoerythrin (PE), a fluorescent particle such as quantum dot, an enzyme such as horseradish peroxidase (HRP) or alkaline phosphatase (AP), a chromophore, or an electrochemically active or a radioactive molecule.

In one embodiment, the detection step comprises a signal development reaction.

In one embodiment the signal development reaction is a chemiluminescent reaction or a colorimetric reaction.

In one embodiment the MNP have a diameter smaller than 50 nm.

In specific embodiments, the MNP have a diameter of 10 nm, 20 nm, 25 nm or 30 nm.

In certain embodiments said assay is used for dot blot analysis, Western blot analysis, slot blot, ELISA or RIA.

In one embodiment said magnetic field is generated by a magnet array composed of small magnets in a chessboard configuration.

In certain embodiments prior to incubating the substrate with the MNP complex, the substrate undergoes blocking with a blocking solution.

In one embodiment, prior to incubating the substrate with a blocking solution, the substrate undergoes a drying step.

The drying step may be performed by heating, air flow, immersion in polar organic solvents, vacuum or any combination thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A shows the vials before applying magnetic field, FIGS. 1B and 1C show the same vials after applying strong magnetic field (surface field 7300 Gauss) for 5 minutes.

FIG. 5A with the standard capture molecule streptavidin-PE, detection exposure time: 4 seconds and FIG. 5B with streptavidin coated 100 nm MNPs, detection exposure time: 15 seconds.

FIG. 11A is a scheme of the experimental setting on the sample membrane, FIG. 11B is a top view picture of a representative device for performing dot blot under a magnetic field, FIG.

11C is a picture of the different elements of the representative device: a neodymium disc magnet, a membrane, and a holder.

Figure 12:
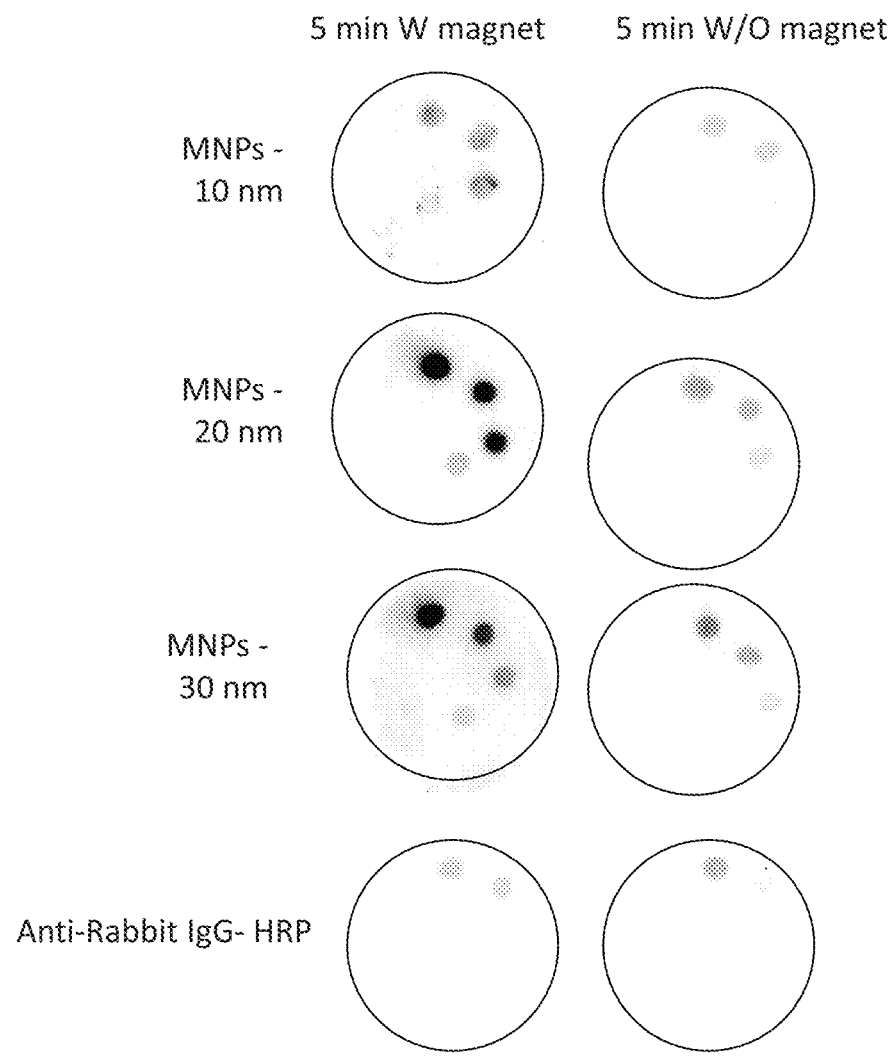

FIG. 12 shows dot blot assays of rabbit IgG with (left panel) and without (right panel) application of magnetic field using: 10 nm MNPs, 20 nm MNPs, 30 nm MNPs (all carrying anti-rabbit IgG-HRP), and free anti-rabbit IgG-HRP.

Figure 13:
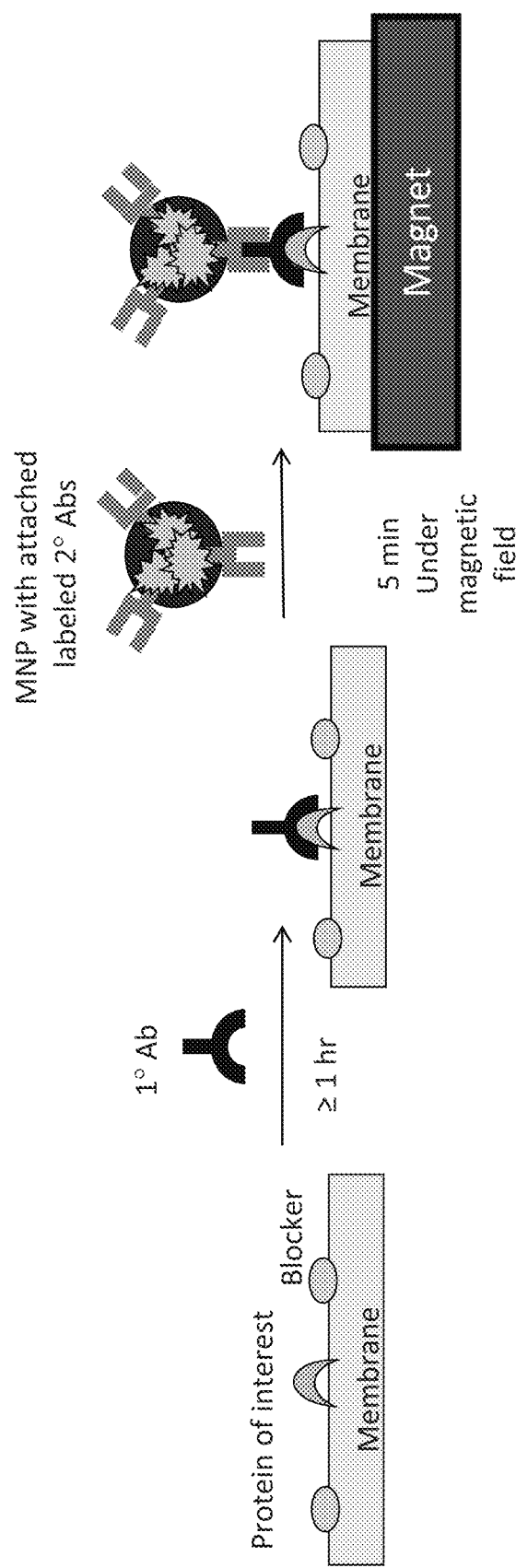

FIG. 13 is a schematic illustration of an assay using separate antibody binding steps.

Figure 14:
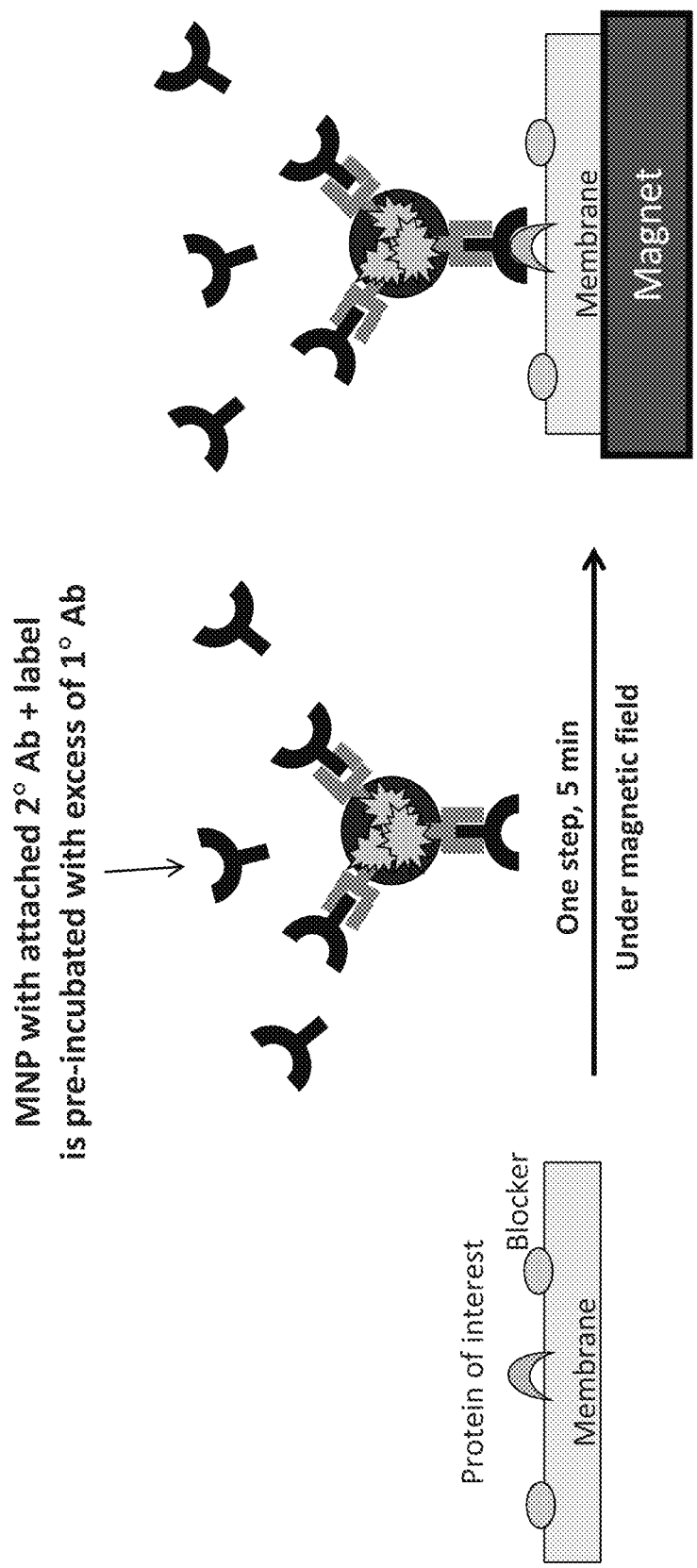

FIG. 14 is a schematic illustration of an assay using combined antibody binding steps. The MNP with the attached secondary antibody and label is pre-incubated with the first antibody prior to performing the assay, for example during electrophoresis.

Figures 15, 16:
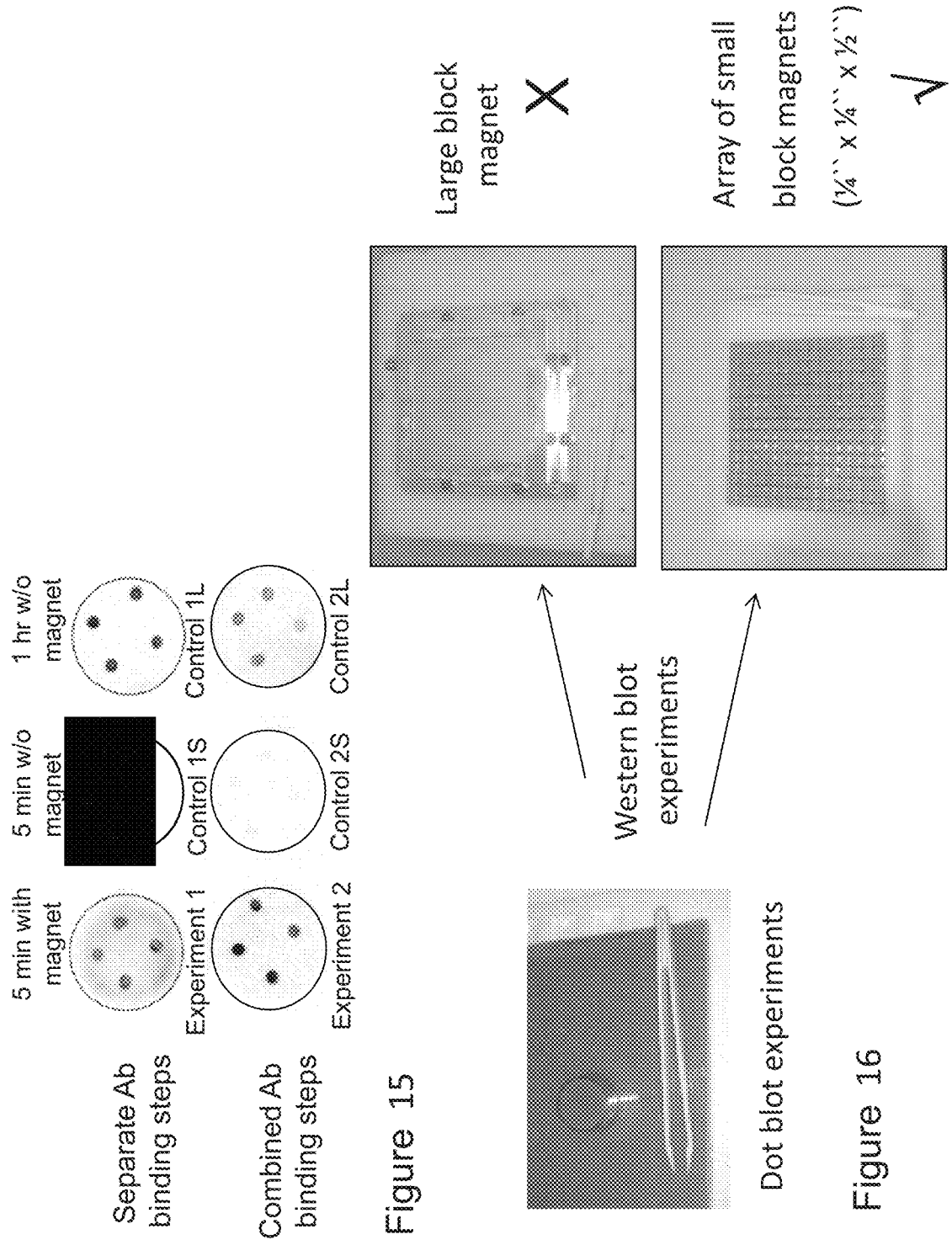

FIG. 15 shows dot blot assays of hT/rabbit anti-hT/MNP-anti-rabbit complex with separate antibody binding steps (upper panel) and combined antibody binding step (lower panel), wherein the assay is with magnetic field for 5 min (left panel), without magnetic field for 5 min (center panel), or without magnetic field for 1 hr (right panel).

FIG. 16 shows the magnetic configurations that were used in the Western blot experiments—the large block magnet and the array of small magnets. The magnet which was used for Dot blot experiments is shown to illustrate the size proportion.

Figure 17:
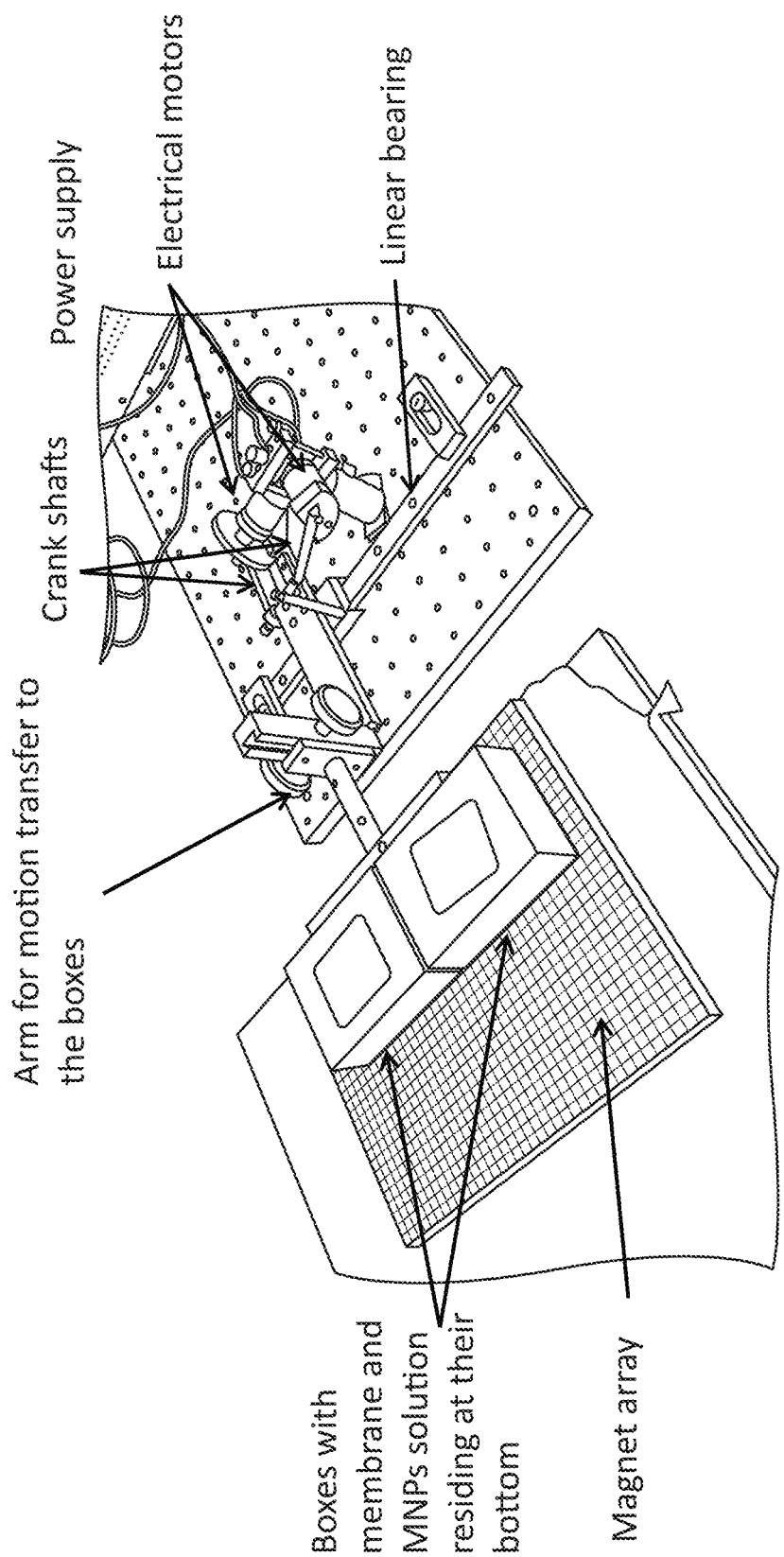
Figure 18A:
Figure 18B:
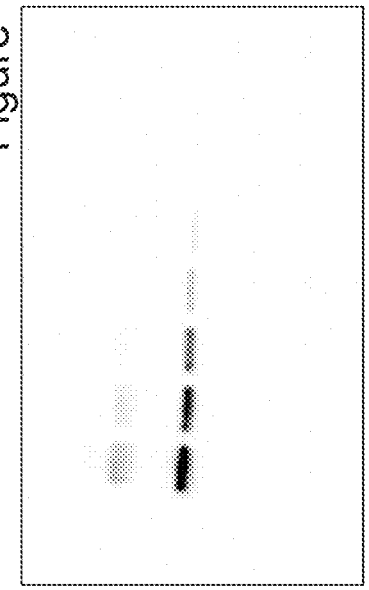
Figure 18C:
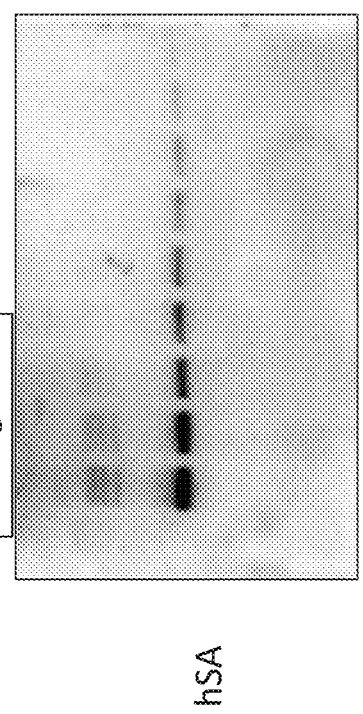
Figure 18D:
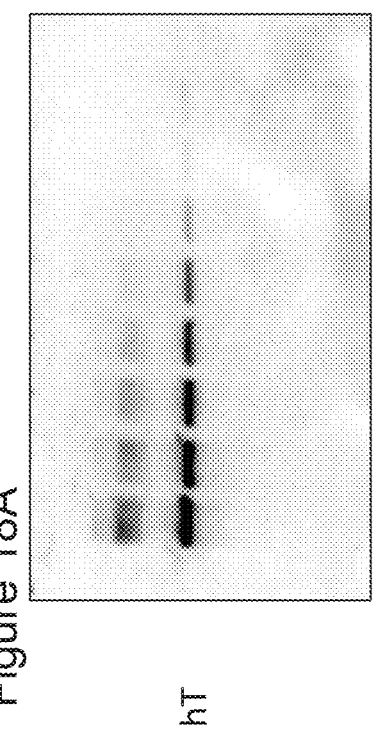

FIG. 17 shows the experimental set up, including a shaker, which was used in the Western blot experiments as described in Examples 7 and 8.

FIG. 18A-D shows the Chemidoc MP images of the MNP-based Western blot experiments as described in Example 7. In these experiments the immunoassay was done as a one 5 min step under magnetic field (A for the hSA model, exposure time: 2 seconds, B for the hT model, exposure time: 3 seconds), vs. reference assay—standard Western blot experiments (C for the hSA model, exposure time: 2 seconds, D for the hT model, exposure time: 3 seconds). The exposure times that were used for the shown images are noted.

Figure 19A:
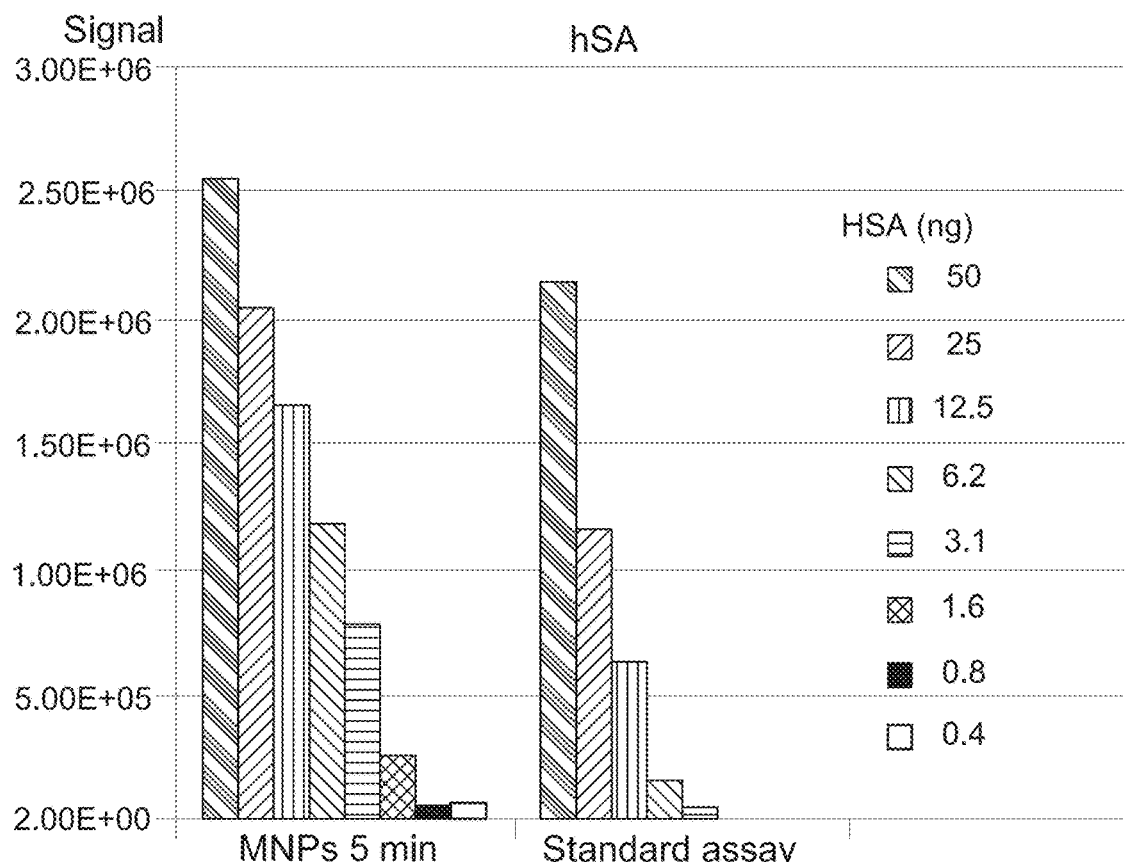
Figure 19B:
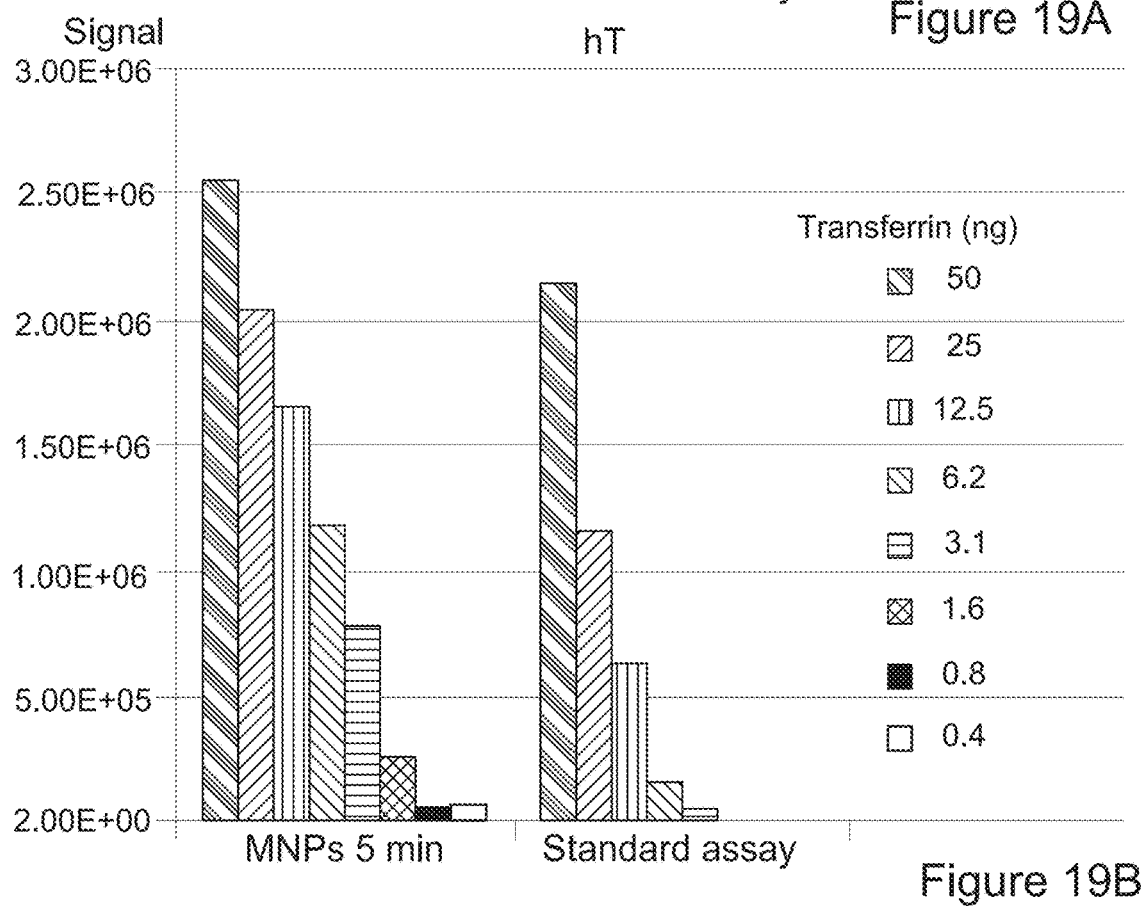
Figure 20D:
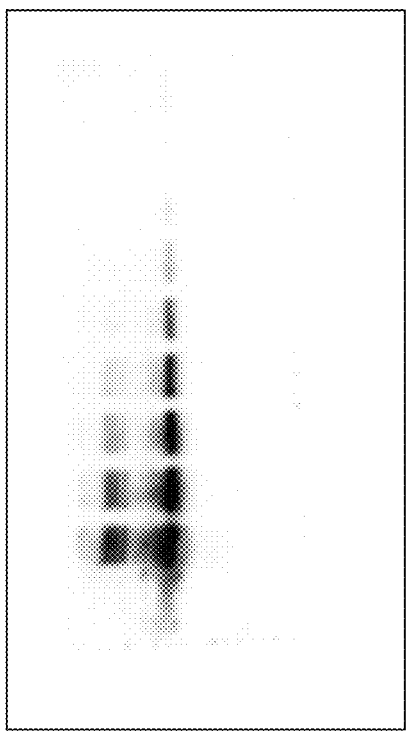
Figure 20D:
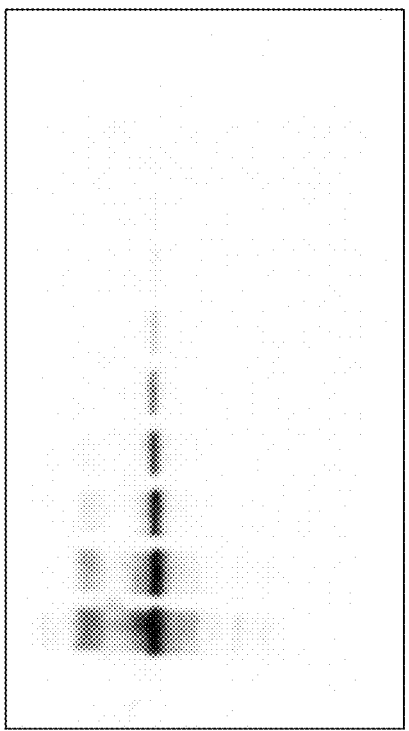
Figure 20D:
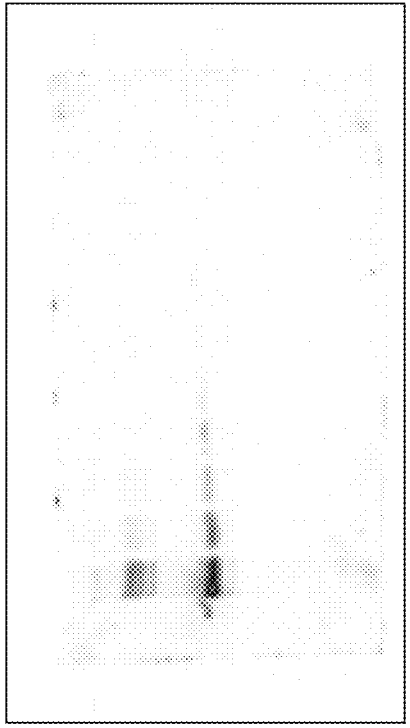
Figure 20D:
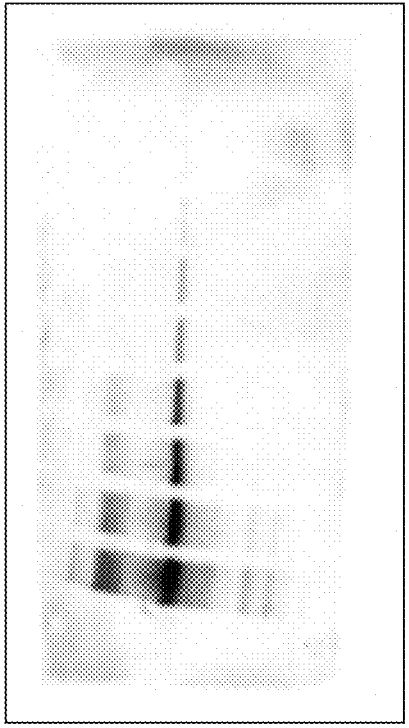

FIG. 19A-B shows the analysis graphs of the images shown in FIG. 18—signal as a function of antigen protein amount (A—for hSA; B—for hT).

FIG. 20A-D shows the Chemidoc MP images of the MNP-based Western blot experiments as described in Example 8. In these experiments the immunoassay was done as a one 5 min step under magnetic field—with membrane drying (C for the hSA model, exposure time: 3 seconds, D for the hT model, exposure time: 5 seconds), or without membrane drying (A for the hSA model, exposure time: 7 seconds, B for the hT model, exposure time: 5 seconds). The exposure times that were used for the shown images are noted.

Figure 21:
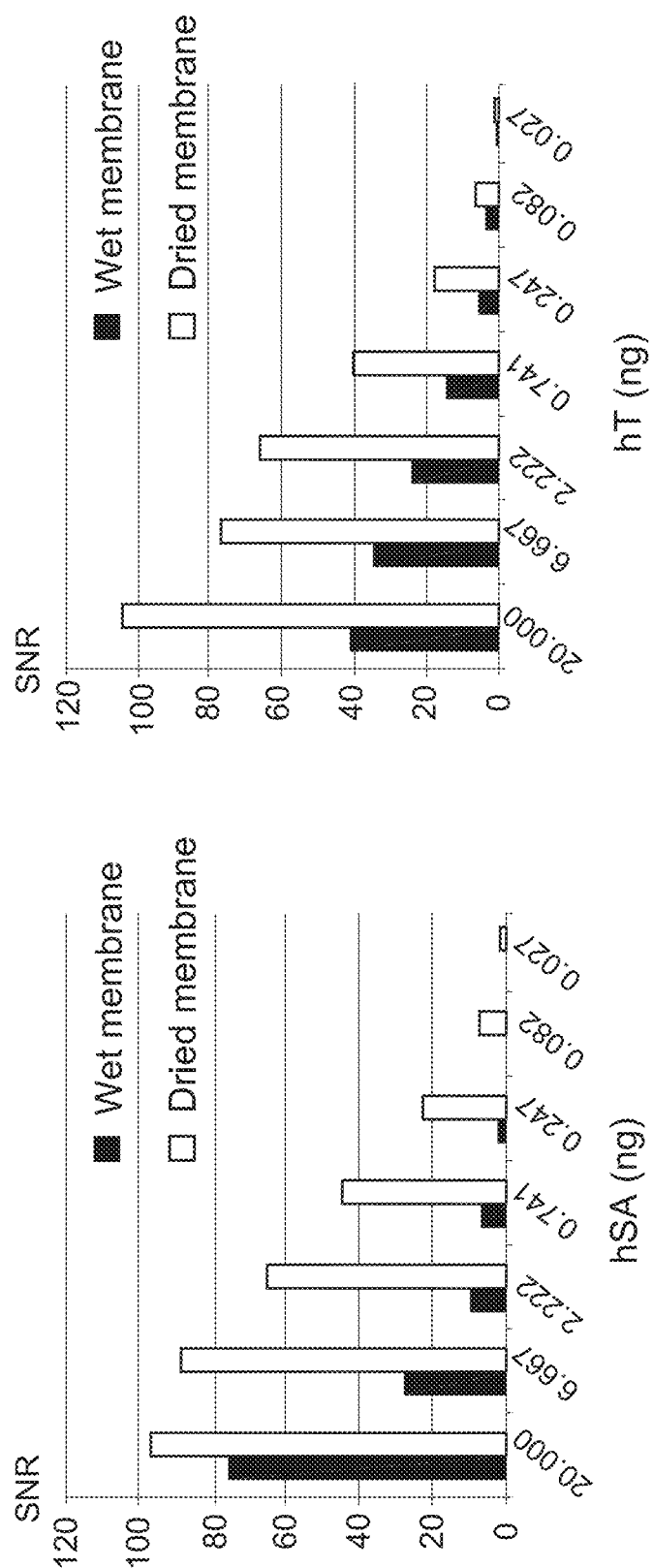

FIG. 21 shows the analysis graphs of the images shown in FIG. 20—SNR as a function of antigen protein amount.

Figure 22:
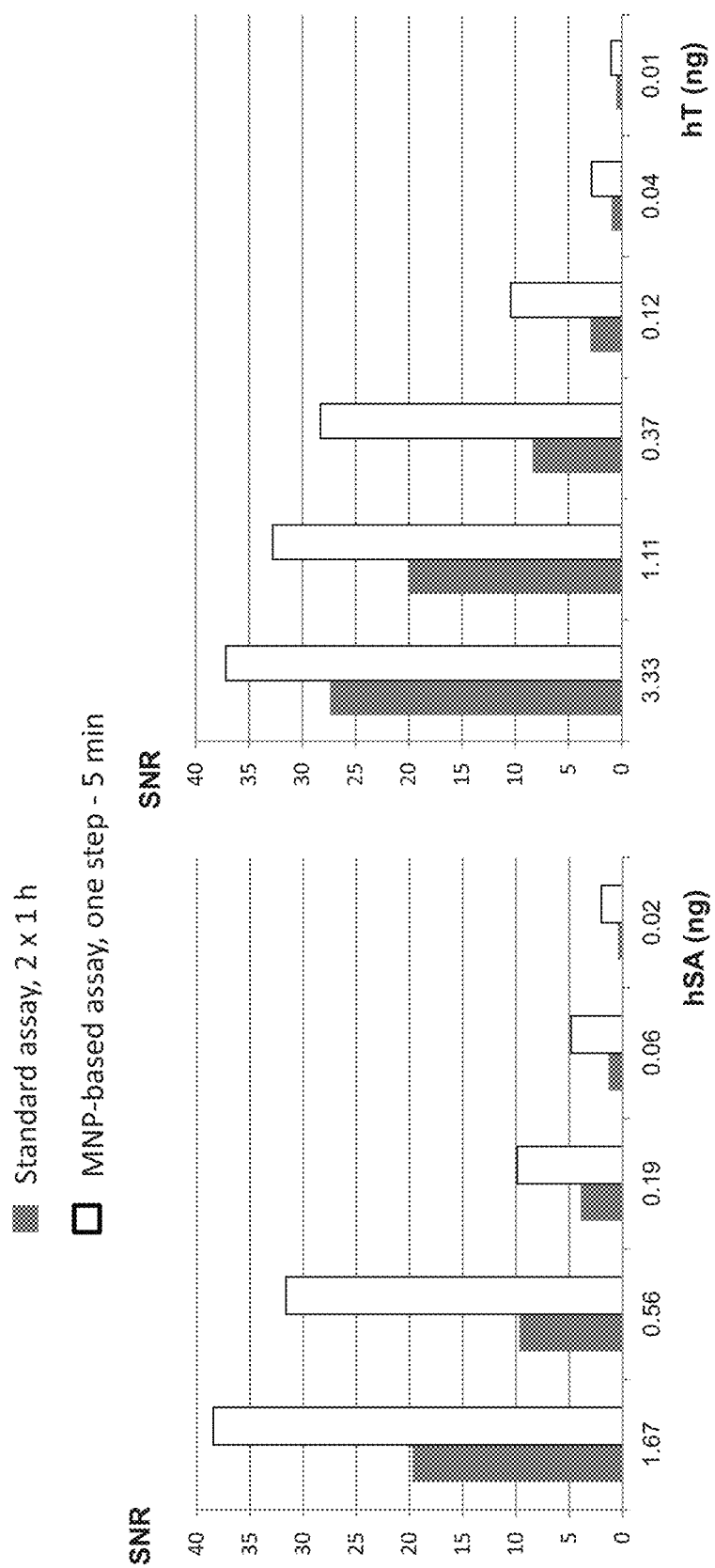

FIG. 22 shows the results of the MNP-based ELISA experiments as described in Example 9, for both the hSA and hT models. In these experiments the immunoassay was done as a one 5 min step under magnetic field vs. reference assay—standard ELISA experiments.

DETAILED DESCRIPTION OF EMBODIMENTS

The present invention provides an immunoassay with enhanced efficiency and speed. The immunoassays of the invention employ small size magnetic nanoparticles that are associated with a capture molecule (a binding agent) and which are detectably labeled. The assay is accelerated by using a magnet.

Figure 1A:
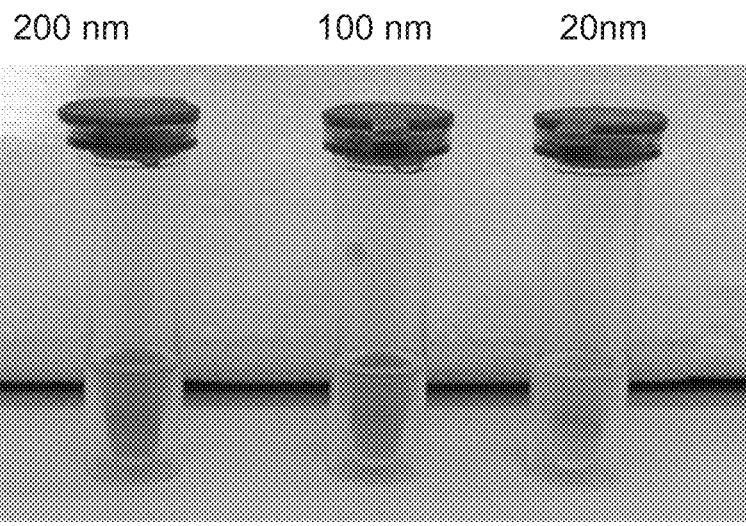
FIG. 1A-C show vials containing MNPs with three different diameters (20 nm, 100 nm and 200 nm)
Figure 1B:
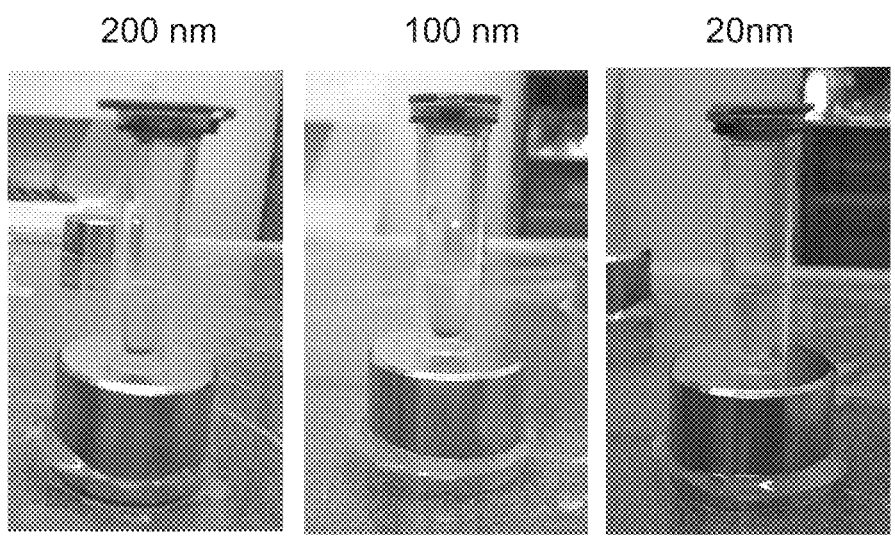
Figure 1C:
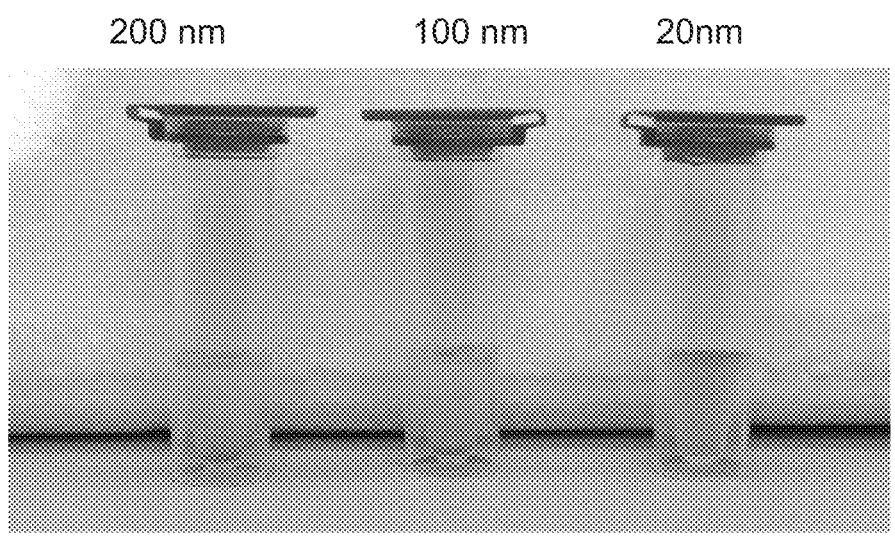

The magnetic susceptibility of MNPs is highly dependent on their size, with lower susceptibility for small MNPs, as shown for example in FIG. 1. MNPs with three different diameters (20 nm, 100 nm and 200 nm) were dissolved in PBS buffer at the same concentration (100 µg/ml) and placed in a vial (FIG. 1A) over a strong magnet (surface field of 7300 Gauss) for 5 min (FIG. 1B). As can be clearly seen in FIGS. 1B and 1C, the 100 nm and 200 nm MNPs were attracted to the magnet, while the solution color of the 20 nm MNPs remained visually unchanged, namely these small MNPs were not attracted significantly to the magnet. Therefore it was surprising that use of these small MNPs provided such effective assay acceleration under the same magnetic field within 5 minutes.

In one embodiment the magnetic nanoparticles of the invention are used for detection of an analyte or a target molecule immobilized on a porous substrate.

In another embodiment the magnetic nanoparticles of the invention are used for detection of an analyte or a target molecule immobilized on a non-porous substrate.

Non-limiting examples of substrate based detection assays are dot blot, slot blot, Western blot and ELISA analyses. These are commonly used assays for detecting the presence and amount of target molecules (usually proteins) in a sample. In a dot blot assay the whole sample which putatively includes the target molecule is placed as such onto a porous substance (e.g. a nitrocellulose membrane) and the proteins within the sample are immobilized in the membrane in the form of a dot.

In a Western blot assay, the sample which putatively includes the target molecule is first run on a separating gel thereby the proteins are separated one from the other and form a gradient according to their size. Next, the separated proteins are blotted onto a nitrocellulose membrane and immobilized onto the membrane according to their respective position in the gel.

In an ELISA (Enzyme-linked immunosorbent assay) the whole sample which putatively includes the target molecule is placed as such onto a non-porous substance (e.g. a well of a standard 96 well plate) and the proteins within the sample coat the bottom of the well. Alternatively, sandwich ELISA assay may be performed. In such case, the bottom of the well is pre-coated with specific primary antibodies directed against a target molecule. Hence the target molecule is immobilized onto the surface via specific binding to these antibodies.

Next, the presence and amount of the target molecule is assessed by an immunoassay conventionally employing a first and a second antibody, whereby the second antibody is detectably labeled so as to detect the presence of the target molecule and its amount.

The examples provided below demonstrate acceleration of the immune-reaction, shortening of assay time and gaining higher assay sensitivity by using the magnetic nanoparticles of the invention.

Accordingly, in one aspect the present invention provides an assay for detecting a target molecule comprising:
  a. Incubating a substrate potentially comprising at least one target molecule with detectably labeled magnetic nanoparticle (MNP) complexes, wherein said MNP complexes comprise MNP having a small diameter associated with a capture molecule capable of binding directly or indirectly to said target molecule;

b. Applying magnetic field; and
c. Subjecting the incubated substrate to a detection step; whereby the presence of a detection signal is indicative of the presence of the target molecule and the signal intensity is indicative of the amount of the target molecule.

In one embodiment, said substrate is a porous substrate, such as a membrane, a filter, a gel, a sponge or any other porous matrix. In one embodiment, the average pore size of the porous substrate is larger than the average diameter of the small MNPs.

In one embodiment, said substrate is a non-porous substrate, such as plastic or glass.

A representative scheme demonstrating one embodiment of the assay is depicted in FIG. 13.

The capture molecule associated with the MNP may be a primary (target) binding agent (e.g. a primary antibody) or a secondary binding agent (e.g. a secondary antibody). The binding agents associated with the MNPs may be detectably labeled. Alternatively, the MNP itself may be detectably labeled.

If the MNPs are associated with a primary binding agent, the assay is performed in a single step whereby the MNPs are directly incubated with the target molecule. Optionally, the target molecule is immobilized on a porous substance.

If the MNPs are associated with a secondary binding agent they may be added to the assay after incubation of the target molecule with a primary target binding agent. Alternatively, the target (primary) binding agent and the magnetic nanoparticles associated with the secondary binding agent may be added simultaneously to the assay vessel containing the target molecule, optionally after a period of incubation. Optionally, the target molecule is immobilized on a porous substance.

A magnet placed under the porous substrate or under the assay vessel causes an accelerated binding reaction as evidenced in the Examples provided below.

Figure 2:
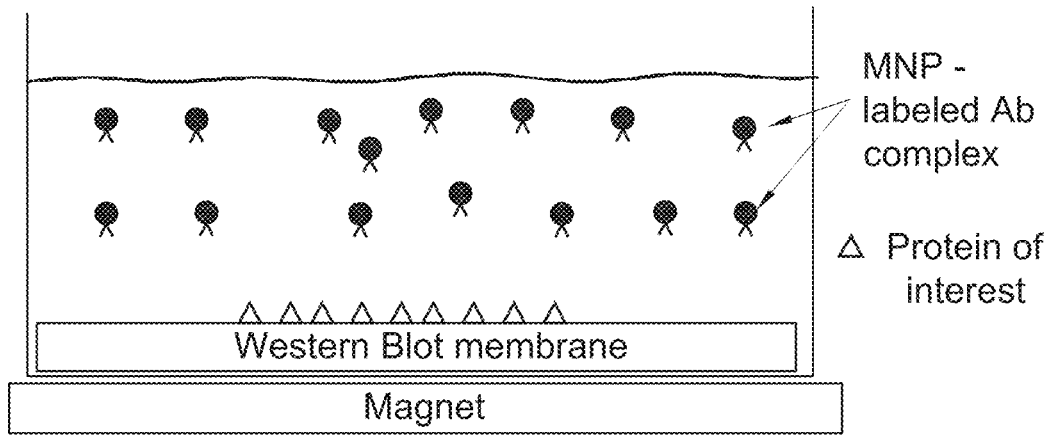
FIG. 2 is a schematic illustration of an assay according to the invention.

FIG. 2 illustrates schematically, in a non-limiting fashion, the general concept of the invention. The figure illustrates different components of the assay of the invention: detectably labeled magnetic nanoparticles associated with an antibody capable of recognizing a target protein, a substrate containing the protein target and a magnet. The binding of the MNPs to the target protein immobilized on the substrate is accelerated via application of magnetic field.

The general concept may be applied to any assay wherein the analyte is immobilized within a porous substrate. Non-limiting examples include a dot blot assay and Western blot analysis. Similarly, the invention can be applied to any assay wherein the analyte is immobilized onto a non-porous substrate either directly or via binding to specific antibodies immobilized onto said non-porous substrate, for example in an ELISA performed in a well-plate.

In accordance with the invention, the detection assay may be performed without separating the steps of (i) binding a primary agent to the target molecule, and (ii) binding a secondary agent to the primary agent. This "combined steps" assay is based on pre-incubation of the MNPs carrying the secondary agent with the primary agent, which is usually in molar excess to assure efficient formation of MNP complexes carrying primary agent. The assay is further based on the enhanced rate of the reaction of the MNP—primary agent complex with the target molecule, which is accelerated by applying magnetic field.

Therefore, in another aspect, the invention provides an assay for detecting a target molecule comprising:

a. Providing a detectably labeled magnetic nanoparticle (MNP) complexes, wherein said MNP complexes comprise MNP associated with a secondary binding agent capable of binding a primary binding agent;
b. Incubating said MNP complexes with a primary binding agent, thereby forming a second MNP complex comprising MNP, a secondary binding agent, and a primary binding agent;
c. Incubating a substrate or a sample potentially comprising at least one target molecule with said second MNP complex;
d. Applying magnetic field; and
e. Subjecting the incubated sample to a detection step; whereby the presence of a detection signal is indicative of the presence of the target molecule and the signal intensity is indicative of the amount of the target molecule.

In one embodiment said MNP has a small diameter.

In one embodiment, said substrate is a porous substrate. In one embodiment, the average pore size of the porous substrate is larger than the average diameter of the small MNPs.

In one embodiment, said substrate is a non-porous substrate.

A representative scheme demonstrating one embodiment of the "combined steps" assay is depicted in FIG. 14.

The term "magnetic nanoparticle complex (MNP complex)" as referred herein relates to a complex comprising one or more magnetic nanoparticles associated with one or more capture molecules. The MNP complex of the invention is detectably labeled. The term "detectably labeled MNP complex" as used herein refers to an MNP complex which is associated with a compound that may be detected by an appropriate reaction (enzymatic or color reaction) or by fluorescent excitation and assists in visualizing, quantifying or detecting the target molecule. Said labeling compound may be associated with the MNP (e.g. formed around the magnetic shell of the MNP) or associated with the capture molecule, or with both.

A non-limiting example of a labeled MNP is an MNP having a shell of lipophilic fluorescence dye which is formed around a magnetic core and coated with a polysaccharide matrix. Capture molecules may be associated (or embedded within) the polysaccharide matrix.

The labeling agent may be a fluorescent compound, e.g. fluorescein (or a fluorescein derivative such as FITC) or phycoerythrin (PE), a fluorescent particle such as quantum dot, an enzyme such as horseradish peroxidase (HRP) or alkaline phosphatase (AP), a chromophore, or an electrochemically active or a radioactive molecule.

The term "Association" or "associated" as used herein refers to any physical or chemical forces such as Van-der-Walls, coordinative, covalent, ionic, electrostatic, dipole-dipole, or hydrogen association (bond or interaction). The association may occur directly or indirectly (i.e. comprising one or more intermediate agents). In some embodiments the intermediate agent is an antibody, another protein, hormone, ligand or spacer. For example, the intermediate agent may be streptavidin, biotin, immunoglobulin binding protein (e.g. protein A, protein G, Protein A/G, protein L, etc.), DNA or RNA molecule, peptide tag or its chelating complex (e.g. polyhistidine tag or metal complex of nitrilotriacetic acid such as Ni-NTA).

The magnetic nanoparticle complexes may be in a dry form (e.g. powder) or dispersed in a medium. The "medium", by its broadest definition, is any material or volume carrying said complexes. In some embodiments the medium may be liquid, gel, or porous material. In some embodiments the medium may be aqueous or non-aqueous liquid.

The term "capture molecule" as used herein refers to an agent which directly or indirectly binds to the target molecule. The capture molecule may be a target binding agent (also referred to as a primary agent) and as such it binds directly to the target molecule. The capture molecule may also be a secondary binding agent which binds to a primary binding agent and as such it binds indirectly to the target molecule via the primary binding agent.

Non-limiting examples of capture agents include antibodies, immunoglobulin binding proteins (e.g. protein A, protein G, Protein A/G, protein L), streptavidin (that binds to biotin and biotin labeled compounds), DNA or RNA strands that bind to complementary DNA or RNA strands, and chelating complexes (such as Ni-NTA) that bind to specific peptide tags (e.g. polyhistidine tag).

The term "target binding agent or primary binding agent", as used herein refers to an agent which specifically associates (binds) to the target molecule (analyte). In some embodiments the target binding agent is a primary antibody directed to the target antigen.

The term "secondary binding agent", as used herein refers to an agent which binds to the target binding agent (the primary agent).

In some embodiments the target binding agent is an antibody which specifically binds the target molecule and the secondary binding agent is a secondary antibody which binds the primary antibody. The primary antibody is specific for the target and may be but is not limited to a mouse antibody, a rabbit antibody, a goat antibody etc. The selection of the type of secondary antibody is dependent on the class of the primary antibody (e.g. IgG or IgD), and on the source of the primary antibody, e.g. if the primary antibody is a mouse antibody, the secondary antibody would be an anti-mouse antibody. The secondary antibody may be detectably labeled. Non-limiting examples of labels include an enzyme (e.g. HRP or AP), a fluorescent compounds (e.g. fluorescein or phycoerythrin), a chromophore, or an electrochemically active or a radioactive molecule.

As used herein the term "second MNP complex" refers to a complex comprising a MNP, a secondary binding agent, and a primary binding agent. Such a complex is obtained by incubating a MNP complex associated with a secondary binding agent with a primary binding agent. The "second MNP complex" may then be applied directly onto the target molecule.

The term "Antibody" as used herein refers to IgG, IgM, IgD, and IgA antibodies. This term refers to whole antibodies or fragments of the antibodies comprising the antigen-binding domain, e.g. scFv, Fab, F (ab')2, bi-specific antibodies, diabodies, and other fragments capable of binding to target molecule. The definition includes polyclonal antibodies and monoclonal antibodies.

"Magnetic nanoparticles" according to the invention encompass any nanoparticle (or nanoparticle material) having magnetism (respond to applied magnetic field) observed therewith. The magnetic nanoparticles may be paramagnetic, ferromagnetic, ferrimagnetic or superparamagnetic nanoparticles.

In some embodiments the magnetic nanoparticle is composed of (or doped with) metal, such as iron (Fe), nickel (Ni), cobalt (Co), manganese (Mn), or any combination thereof. In some embodiments the magnetic nanoparticle is composed of rare earth metal, such as gadolinium (Gd), neodymium (Nd), samarium (Sm), dysprosium (Dy), Holmium (Ho), or any combination thereof.

In some embodiments the material is an alloy of metals, wherein at least one metal is having magnetism. In some embodiments the alloy is steel, Neodymium-iron-boron alloy ($Nd_2Fe_{14}B$), nickel-iron alloy (also known as Permalloy), aluminum-nickel-cobalt alloy, samarium-cobalt alloy, yttrium-iron alloy (YIG), yttrium-cobalt alloy ($YCo_5$).

In some embodiments the magnetic nanoparticles are composed of metal oxide. Non-limiting examples are iron oxides, such as $Fe_2O_3$, $Fe_3O_4$, FeO, manganese oxide, such as, $Mn_3O_4$, $Mn_2O_3$, and oters, such as, $CrO_2$, EuO, or any combination thereof.

In some embodiments the magnetic nanoparticles are composed of minerals. Non-limiting examples of magnetic minerals are $FeS_2$, $Fe_3Si$.

In some embodiments, the magnetic nanoparticles are materials (magnetic or non-magnetic, e.g., metals, semiconductors, insulators) doped with a magnetic component. In some embodiments the magnetic nanoparticles are composed of a semiconductor material doped (or alloyed) with magnetic material. e.g., GaAs, In As, InSb, AlN, $TiO_2$, ZnO, $SnO_2$ doped with one or more of the following dopants (atoms or ions) Fe, Co, Ni, Cr, Mn, V.

In some further embodiments, the magnetic nanoparticles are composed of a semiconductor material, such as MnAs, MnSb.

In some embodiments the magnetic nanoparticles are composed of iron oxide.

The magnetic nanoparticle in accordance with the present invention has dimensions (length or diameter) at the nanometric range (between 1 and 1000 nm). In some embodiments, the nanoparticles of the invention are small sized nanoparticles being in the range of between 1 nm to 50 nm in length or diameter. In some specific embodiments, the nanoparticles are on average in the range of 1 nm to 30 nm in length or diameter. In other embodiments, the nanoparticles are on average in the range of 10 nm to 30 nm in length or diameter. In specific embodiments the nanoparticles have a diameter of 10 nm, or 20 nm, or 25 nm, or 30 nm.

In some embodiments, the nanoparticles are selected amongst isotropic and anisotropic shaped nanoparticles. Without being limited thereto, the nanoparticles may be symmetrical or unsymmetrical, may be elongated or having a round (spherical)-shape, rod-like shape, elliptical, branch, network or any irregular shape. In some embodiments, the nanoparticles are selected from nanospheres, nanorods, branched nanoparticles, multipods and others. In one specific embodiment, the labeled MNP complex in accordance with the invention is a small sized iron oxide nanoparticle (≤30 nm) coated with linear amphiphilic polymer carrying end carboxylic groups associated with horseradish peroxidase (HRP)-labeled anti-rabbit IgG secondary antibody.

The assay of the invention may be a Western blot assay. Protocols for carrying out Western blot assays are well known in the art. In general a first step in a Western blot assay is electrophoresis of a sample containing the target molecules. Typically electrophoresis is carried out on polyacrylamide gels. A non-limiting example of a protocol for carrying out a Western blot assay is provided in Example 7 below. Following electrophoresis the target molecules are transferred onto a porous substrate for further analysis.

The system of the invention operates on the basis of acceleration of magnetic nanoparticle complexes, carrying the capture agent to a substrate containing the target molecule. The substrate may be a porous substrate. As used herein, the term "porous substrate" refers to a substrate having a plurality of pores (depressions). These pores have inner voids of the same or varying volume and shape, defined by inner surface. The substrate pores are nanometric in size, namely having a mean size smaller than 1,000 nm. In some embodiments, the mean pore size is below 500 nm. In other embodiments, the mean pore size is below 300 nm. In further embodiments, the mean pore size is below 200 nm. In other embodiments, the mean pore size is below 100 nm. In other embodiments, the mean pore size is below 50 nm. In further embodiments, the mean pore size is between 300 nm and 50 nm. In specific embodiments the porous substrate is a membrane having 200 nm or 450 nm pores.

The substrate may also be a non-porous substrate.

The substrate may be a flexible or a rigid or a soft substrate, and may be composed of any material. In some embodiments the substrate is a layered substrate, e.g., a porous layer on a non-porous layer or soft layer (such as gel or tissue) on metal layer (holder). The substrate (or one of its layers) may be composed of insulating, conducting or semi-conducting material. In some embodiments the substrate may be composed of glassy, polymeric, ceramic, fibrous material, or any combination thereof. In some embodiments the substrate's material may be composed of glass, paper, wool, fleece, gel, cellulose, or any combination thereof. In some embodiments the substrate is composed of a nitrocellulose or PVDF membrane. The nitrocellulose or PVDF membrane may have varying pore sizes, e.g. 0.2 μm (200 nm) or 0.45 μm (450 nm).

One or more of the target molecules is associated to (immobilized on) the surface of the substrate. The "target molecule" or "analyte" (used herein interchangeably) refers to any agent whose presence and/or amount is to be determined. In some embodiments the target molecule may be a mixture of several target molecules. In some embodiments the presence or concentration profile of the different target molecules is to be determined.

The target molecule may be any biological and/or chemical agent (i.e., molecule/macromolecule/complex/conjugate). In some embodiments the target molecule is an organic or inorganic molecule. In some embodiments the target molecule is a biological agent.

In one embodiment the target molecule is a protein, a polypeptide or a peptide. In some other embodiments the target molecules are nucleic acids (e.g. DNA, RNA), carbohydrates, lipids, glycolipides, triglyceride or polysaccharide. The target molecules may be hormones, vitamins, antibodies, metabolites, amino acid (e.g., glutamic acid, aspartic acid), alcohol (e.g., ethanol), organic acid (e.g., acetic acid, lactic acid), antioxidant (e.g., ascorbic acid), polyol (e.g., glycerol) or any derivatives and/or combination thereof. In some embodiments the target molecule is a toxin or a drug. In some embodiments the assay of the invention may detect even small amounts of the target molecule. In some embodiments amount of the target molecule in the substrate is in micrograms. In some embodiments the amount of the target molecule is below 1 microgram. In some embodiments amount of the target molecule in the substrate is in nanograms. In some embodiments the amount of target agent in the substrate is between 100 ng to 1 ng. In some embodiments the amount of target agent in the substrate is between 100 pg to 1 pg.

The system of the invention comprises an element generating magnetic field, i.e., a magnet. The system of the invention may have one or more magnets. In some embodiments, the system has at least one magnet situated in vicinity to the substrate. In some embodiments, the magnet is positioned below the substrate. In other embodiments, the magnet may be positioned on top of the substrate or on the side. The magnet may be a permanent magnet or an electromagnet.

The size of the magnet is selected according to the size of the substrate used in the assay. In some non-limiting embodiments, the element generating a magnetic field is a magnet array composed of small magnets (e.g. ¼ inch×¼ inch×½ inch, as shown in FIG. 16). The magnetic polarity in the magnet array may be perpendicular, namely intersecting at a right angle to the main plane formed by the magnets, and opposite for each neighboring magnet (i.e. a chessboard configuration), also termed herein a "chessboard magnet array".

In some embodiments, the assay of the invention further comprises a detection step. In some embodiments, the detection step may involve illuminating said substrate followed by fluorescent detection (e.g. by using a fluorescent imager), densitometry measurements, spectrophotometer measurements, light scattering measurements, current measurements, magnetic induction measurements, light detection (by e.g. a CCD camera, photographic film) or radioactivity detection. In some embodiments, the assay of the invention comprises label free detection based on mass or refractive index change, such as surface plasmon resonance (SPR) or quartz crystal microbalance (QCM).

In some embodiments, the detection step comprises a signal development reaction. In a specific embodiment, the signal development reaction is a chemiluminescent reaction, which is catalyzed by the labeling agent on the substrate. For example, the chemiluminescent reaction of lumiunol is catalyzed by the enzymes HRP or AP under suitable conditions, which are provided in standard chemiluminescence development solutions. In another specific embodiment, the signal development reaction forms a detectable color. For example, the colorimetric reaction of several reagents, such as TMB or OPD, is catalyzed by HRP under suitable conditions.

In accordance with one aspect of the invention the assay is performed with a substrate comprising at least one target molecule. In some embodiments the substrate comprising (or associated with) at least one target molecule is formed by contacting a sample potentially comprising the target molecule with the substrate. In one embodiment, the target molecules are deposited on the surface of the substrate, which may be a porous substrate, and through surface opening(s) of the substrate one or more target molecules are immobilized onto the inner surface of the substrate's pores. Alternatively, the substrate may be a non-porous substrate. In such case the substrate's surface is being coated by the target molecules, either directly or indirectly via binding to a specific antibody which is immobilized onto the substrate's surface. The target molecule may be deposited on the substrate by any method. In some embodiments, deposition may be by simple dropping a sample containing the target molecule on the substrate or immersing the substrate in the sample. In some embodiments, the substrate may be activated prior to the exposure to the target molecules, for example surface carboxylic acid groups are commonly activated by a solution containing EDC and NHS to enable standard amine coupling. In some embodiments the substrate (e.g. a nitrocellulose membrane) is brought into close proximity with a gel carrying the target molecule whereby the target molecule is transferred (blotted) from the gel onto the nitrocellulose or PVDF membrane. In some embodiments, the sample comprising the target molecule(s) is deposited on a substrate by employing electrochemical deposition, electrophoretic deposition, electroplating, spraying, spin coating, or any other method of deposition.

In some embodiments, prior to contacting the magnetic nanoparticle complexes of the invention with the substrate comprising the target molecule, the substrate may undergo one or more treatments steps, such as washing, drying, blocking, heating or de-activation. In some embodiments, said treatment step is blocking. In some embodiments the blocking treatment is performed by placing (or immersing) the substrate in blocking solution, which may contain proteins (e.g. non-fat milk or BSA), buffer (e.g. Tris Buffered Saline (TBS) or Phosphate Buffered Saline (PBS)), and detergent (such as Tween 20 or Triton X-100).

In some embodiments, the assay may include a drying step (i.e. a step of water exclusion or partial water exclusion) in which the substrate (e.g. the membrane) is dried prior to incubating the substrate with the MNP complex, and in particular, prior to the blocking step that precedes the incubation with the MNP complex. Drying of the membrane improves the Signal to Noise Ratio (SNR), namely higher signals and lower background are obtained in assays that include membrane drying. Without wishing to be bound by theory, the higher signals are probably due to fixation of the target proteins to the membrane, and preventing loss of proteins during the following assay and wash steps. The lower background is probably due to more efficient blocking—the blocking proteins are brought into the membrane by wetting process, which is much faster and efficient than diffusion process as in the standard blocking.

Membrane drying may be performed using any method known in the art, for example by heating, subjecting to air flow, immersion in polar organic solvents (e.g. alcohol or DMSO), applying vacuum or any combination thereof.

In one specific embodiment drying is performed by placing the membrane in a laboratory oven at 37° C. under air flow for 30 min.

In some embodiments, some or all of the assay steps (such as, depositing the target molecule onto the substrate, permitting association of a primary binding agent to the target molecule, contacting at least one magnetic nanoparticle complex or medium containing such a complex with the substrate etc.) may have prior and/or post steps of washing. In some embodiments, the washing step is by placing (or immersing) the substrate in a washing solution. In some embodiments, the washing solution comprises buffer (e.g. TBS or PBS) and a detergent (such as Tween 20 or Triton X-100). In some embodiments, the washing of MNPs from the substrate surface may be accelerated or made more efficient by magnetic attraction. For that, the magnet should be positioned at an opposite direction to the direction that was used to accelerate the MNP-analyte binding reaction. For example, if the magnet was placed below the membrane for the binding step, it should be placed above the membrane in the washing step. Alternatively, the membrane may be rotated with its upper face down while the magnet remains below the membrane.

In some embodiments, the assay comprises separation of the magnetic nanoparticle complexes from the other agents in the medium. For example, if the MNP complex is mixed with excess of primary binding agent, it may be useful to purify the MNP complexes that bound the primary binding agent and wash away the excess of primary binding agent. The magnetic properties of the MNPs may be used for the separation. Non-limiting examples of separation means is by magnetic precipitation, or passing through a magnetic column. Alternatively, common methods for separation by size may be used, such as centrifugation, chromatography or filtering.

Outlined below are several embodiments of the invention:

In one specific embodiment the invention provides a dot blot assay comprising the steps of:
  a. blotting the target molecule onto a membrane;
  b. incubating the membrane with MNPs having a small diameter conjugated to a labeled target binding agent while applying a magnetic field; and
  c. detecting the label.

In another specific embodiment the invention provides a dot blot assay comprising the steps of:
  a. blotting the target molecule onto a membrane;
  b. immersing the membrane in a blocking solution;
  c. incubating the membrane with a target binding agent;
  d. incubating the membrane with MNPs having a small diameter conjugated to a labeled secondary agent while applying a magnetic field; and
  e. detecting the label.

A schematic representation of this embodiment is outlined in FIG. 13.

In another specific embodiment the invention provides a dot blot assay comprising the steps of:
  a. blotting the target molecule onto a membrane;
  b. immersing the membrane in a blocking solution;
  c. immersing the membrane in a pre-prepared solution containing a primary binding agent (e.g. a primary antibody) and MNPs having a small diameter associated with a labeled secondary agent (e.g. a secondary antibody) while applying a magnetic field; and
  d. detecting the label.

A schematic representation of this embodiment is outlined in FIG. 14.

In another specific embodiment the invention provides a Western blot assay comprising the steps of:
  a. subjecting a sample comprising proteins to electrophoretic separation;
  b. transferring (i.e. blotting) the separated proteins to a membrane;
  c. immersing the membrane in a blocking solution;
  d. immersing the membrane in a pre-prepared solution containing a primary binding agent (e.g. a primary antibody) and MNPs having a small diameter associated with a labeled secondary agent (e.g. a secondary antibody) while applying a magnetic field; and
  e. detecting the label.

In another specific embodiment the invention provides a Western blot assay comprising the steps of:
  a. subjecting a sample comprising proteins to electrophoretic separation;
  b. transferring (i.e. blotting) the separated proteins to a membrane;
  c. immersing the membrane in a blocking solution;
  d. incubating the membrane with a target binding agent;
  e. incubating the membrane with MNPs having a small diameter conjugated to a labeled secondary agent while applying a magnetic field; and
  f. detecting the label.

In another specific embodiment the invention provides a Western blot assay comprising the steps of:
  a. subjecting a sample comprising proteins to electrophoretic separation;
  b. transferring (i.e. blotting) the separated proteins to a membrane;
  c. drying the membrane;
  d. immersing the dried membrane in a blocking solution;

e. immersing the membrane in a pre-prepared solution containing a primary binding agent (e.g. a primary antibody) and MNPs having a small diameter associated with a labeled secondary agent (e.g. a secondary antibody) while applying a magnetic field; and f. detecting the label.

In another specific embodiment the invention provides a Western blot assay comprising the steps of:

a. subjecting a sample comprising proteins to electrophoretic separation;

b. transferring (i.e. blotting) the separated proteins to a membrane;

c. drying the membrane;

d. immersing the dried membrane in a blocking solution;

e. incubating the membrane with a target binding agent;

f. incubating the membrane with MNPs having a small diameter conjugated to a labeled secondary agent while applying a magnetic field; and g. detecting the label.

In another specific embodiment the invention provides an ELISA comprising the steps of:

a. coating the substrate with the target protein;

b. adding a blocking solution;

c. adding a pre-prepared solution containing a primary binding agent (e.g. a primary antibody) and MNPs having a small diameter associated with a labeled secondary agent (e.g. a secondary antibody) while applying a magnetic field; and d. detecting the label.

In another specific embodiment the invention provides an ELISA comprising the steps of:

a. coating the substrate with a first primary binding agent (e.g. a first primary antibody);

b. adding a blocking solution;

c. adding the target protein;

d. adding a pre-prepared solution containing a second primary binding agent (e.g. a second primary antibody) and MNPs having a small diameter associated with a labeled secondary agent (e.g. a secondary antibody) while applying a magnetic field; and e. detecting the label.

In another specific embodiment the invention provides an ELISA comprising the steps of:

a. coating the substrate with the target protein;

b. adding a blocking solution;

c. adding a primary binding agent (e.g. a primary antibody);

d. adding MNPs having a small diameter conjugated to a labeled secondary agent (e.g. a labeled secondary antibody) while applying a magnetic field; and e. detecting the label.

In another specific embodiment the invention provides an ELISA comprising the steps of:

a. coating the substrate with a first primary binding agent (e.g. a first primary antibody);

b. adding a blocking solution;

c. adding the target protein;

d. adding a second target binding agent (e.g. a second primary antibody);

e. adding MNPs having a small diameter conjugated to a labeled secondary agent while applying a magnetic field; and f. detecting the label.

Preferably the first and the second primary binding agents are directed against different binding sites on the target molecule.

In another aspect the invention provides a detectably labeled MNP complex comprising magnetic nanoparticles having a small diameter associated with a capture molecule capable of binding directly or indirectly to a target molecule, for use in an assay for the detection of said target molecule wherein said target molecule is immobilized onto a porous substance. In another embodiment said target molecule is immobilized onto a non-porous substance.

In some embodiments, the detectably labeled MNP complex is for use in research laboratories, hospitals or medical care centers (for the professional user, such as a technician, a nurse, a doctor). In some embodiments, the detectably labeled MNP complex is for home use (for by patients).

The invention is demonstrated in the following examples.

EXAMPLES

Example 1

Dot Blot Analysis Using 100 Nm Fluorescent MNP-Capture Agent Complexes

Figure 3:
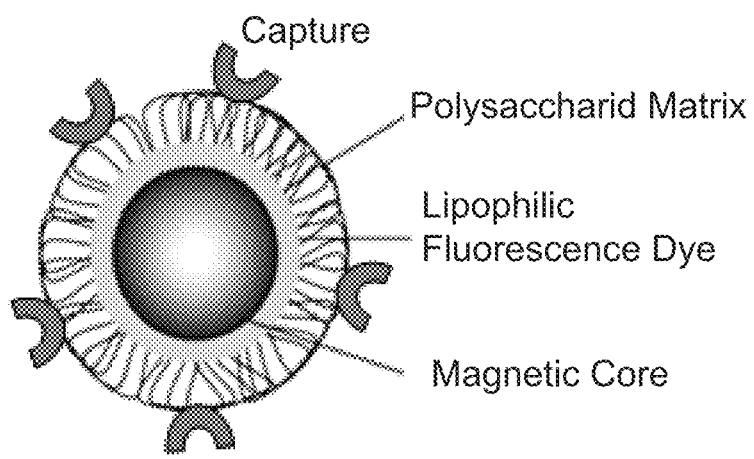
FIG. 3 is a schematic depiction of an exemplary MNP complex having average diameter of 100 nm.

Fluorescent magnetic nanoparticles (MNPs) of 100 nm size (hydrodynamic diameter) were purchased from Chemicell. These MNPs contain a shell of lipophilic fluorescence dye which was formed around a magnetic core and coated with a polysaccharide matrix. Capturing agents were embedded within the polysaccharide matrix (FIG. 3). MNPs with three capture agents—Protein G, anti-mouse IgG and streptavidin—were tested. All three MNP types had fluorescence with excitation pick at 547 nm and emission pick at 580 nm.

Figure 4:
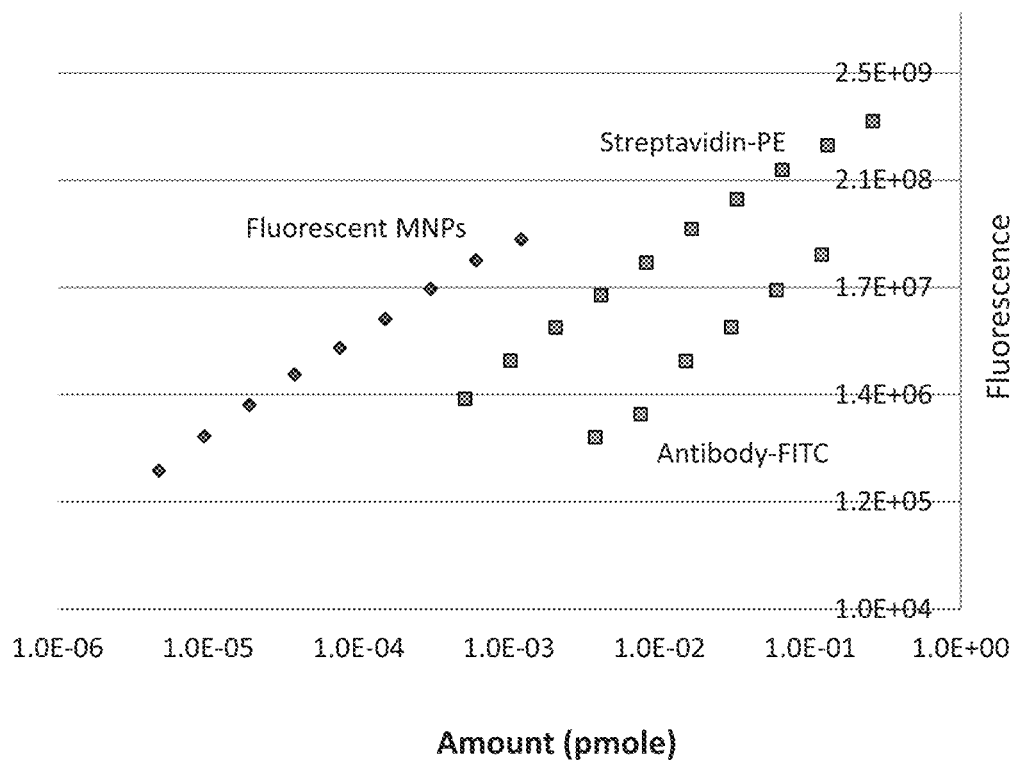
FIG. 4 shows the fluorescent signal of 100 nm MNPs, as compared with fluorescently labeled standard capture molecules streptavidin-PE (phycoerythrin) and antibody-FITC (fluorescein isothiocyanate) as a function of amount in dots on a membrane.

Preliminary experiments were done to evaluate the fluorescence level of these MNPs. Small drops (2 μl) of solutions containing MNPs at a series of concentrations were spotted over a 0.45 μm nitrocellulose (NC) membrane. Similar spotting was done with standard capturing agents that were labeled with the commonly used fluorophores fluorescein (as FITC) and phycoerythrin (PE). Fluorescent detection was done using ChemiDoc MP Imager (Bio-Rad). It was shown that the molar fluorescence of the MNPs is much higher than that of the standard capturing agents (FIG. 4).

Figures 5A, 5B:
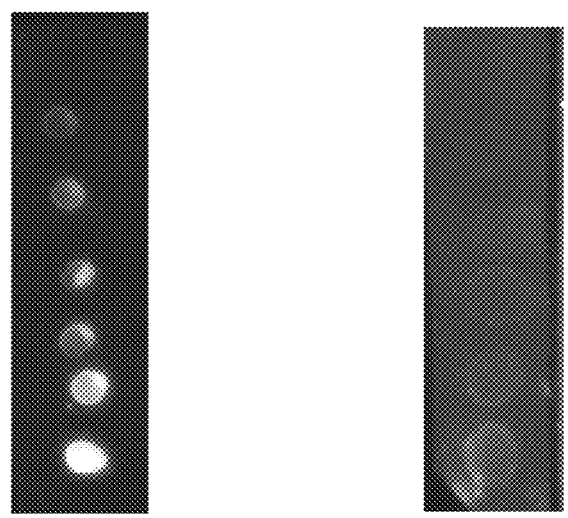
FIG. 5A-B show dot blot assay of the reaction of a biotinylated protein.

It was thus expected that the MNPs would provide stronger (or at least comparable) signals than the standard captures in dot blot experiments, namely in immune-reaction with an antigen which was spotted onto the membrane. However, the results of dot blot experiments indicated that the MNPs failed to function as good as the standard capturing agents. For example, 2 μl drops of biotinylated antibody at a series of concentrations were spotted on 0.45 μm NC membranes. One membrane was then exposed to a solution of streptavidin coated MNPs, and a second reference membrane was exposed to the standard capture streptavidin-PE under similar conditions (e.g. the same molar concentration). Detection using the ChemiDoc MP imager revealed strong signals with streptavidin-PE (FIG. 5A) and only weak signals with streptavidin-MNP (FIG. 5B).

Similar results were recorded when the other MNP types (with Protein G or anti-mouse IgG) were compared to standard labeled captures. Applying magnetic field in order to enhance the MNP-based detection did not improve the results.

An apparent conclusion from these experiments is that the binding of MNPs to the antigens, which were adsorbed to the porous membrane, is not efficient comparing to standard capture molecules. Without wishing to be bound by theory, this low binding may be due to the large size of the examined MNPs which limits their membrane penetration. Accordingly, in the following examples smaller MNPs were used.

Example 2

Characterization of Smaller (≤30 nm) MNP-Antibody Complexes

Figure 6:
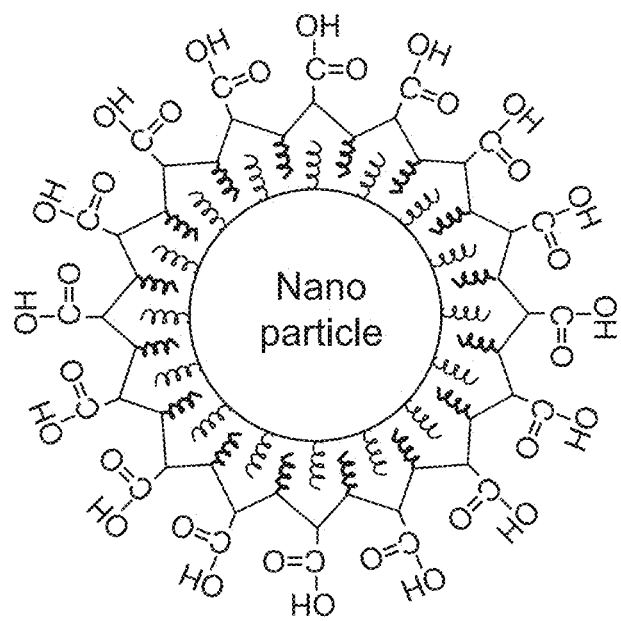
FIG. 6 is an illustration of exemplary small MNPs (average diameter <50 nm). The figure shows an illustration of water soluble IO nanoparticles with amphiphilic polymer surface coating.

To overcome the disadvantages of the system described in Example 1, magnetic nanoparticle-antibody complexes comprising small sized iron oxide nanoparticles 30 nm) were purchased from Ocean Nanotech. These iron oxide (IO) nanoparticles are coated with linear amphiphilic polymer carrying end carboxylic groups, which can be used to immobilize antibodies or other proteins (FIG. 6).

IO magnetic nanoparticles associated with horseradish peroxidase (HRP)-labeled anti-rabbit IgG secondary antibody (Ocean Nanotech) were used in the following experiment. Three nanoparticle sizes were used: 10 nm, 20 nm, and 30 nm. Enzyme (HRP) activity of the nanoparticles was tested using a colorimetric assay in solution, with comparison to the free labeled antibody (anti-rabbit IgG-HRP from Jackson). This analysis was done by placing a concentration series of MNP or antibody solution in wells of non-binding 96 well plate (50 μl solution per well). Color development was done by adding 100 μl of standard TMB solution to each well, and was stopped by adding 50 μl sulfuric acid. The signal was detected by reading optical density at 450 nm ($OD_{450}$) using a plate reader.

Figure 7:
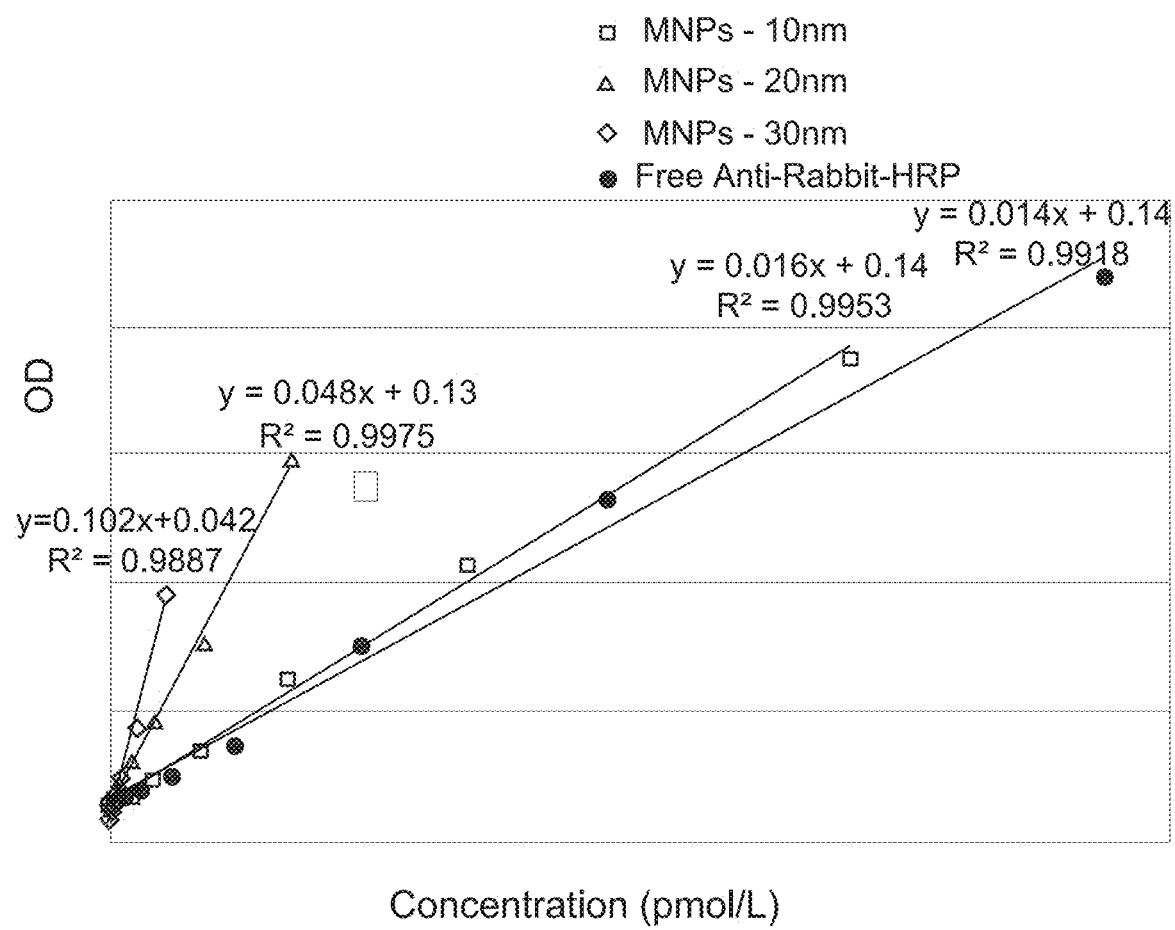
FIG. 7 shows graphs of optical density (OD) at 450 nm wave length indicative for HRP-catalyzed color formation, as a function of concentration of: anti-rabbit IgG-HRP labeled 10 nm MNPs, 20 nm MNPs, 30 nm MNPs, or free anti-rabbit IgG-HRP.

The results are presented in FIG. 7, wherein the $OD_{450}$ is shown as a function of the labeled MNP/antibody concentration. High activity was observed with all the tested MNPs, while all MNPs were found to be more active than the free anti-rabbit HRP (in molar terms). The magnetic particles-associated with anti-rabbit-HRP showed higher molar activity with increasing magnetic particles diameter. By using the slope values as indicated in FIG. 7, and the value recorded for the free anti-rabbit HRP as reference, the average number of antibody molecules per MNP is estimated to be about 1.5, 4.5 and 9.6 for the 10, 20 and 30 nm MNPs, respectively. Apparently, the larger particles can carry a larger number of antibody molecules per particle, and hence their increased enzymatic activity.

Example 3

Dot Blot Analysis with Small MNPs Carrying a Secondary Antibody

Dot Blot Assay with Rabbit IgG/Anti Rabbit IgG Antibody
Rabbit IgG solution (2 μl) was spotted on two 0.45 μm NC membrane at a series of 16 concentrations (×1.5 dilution series), yielding spotted amounts from 5 μg down to 11 ng. One membrane was reacted with the 10 nm IO magnetic nanoparticles described in Example 2 (0.43 nM). The second, reference membrane was reacted with free anti-rabbit HRP under similar conditions (e.g. the same molar concentration). Color signal was developed and detected using 4-CN substrate and ChemiDoc MP imager.

Figure 8:
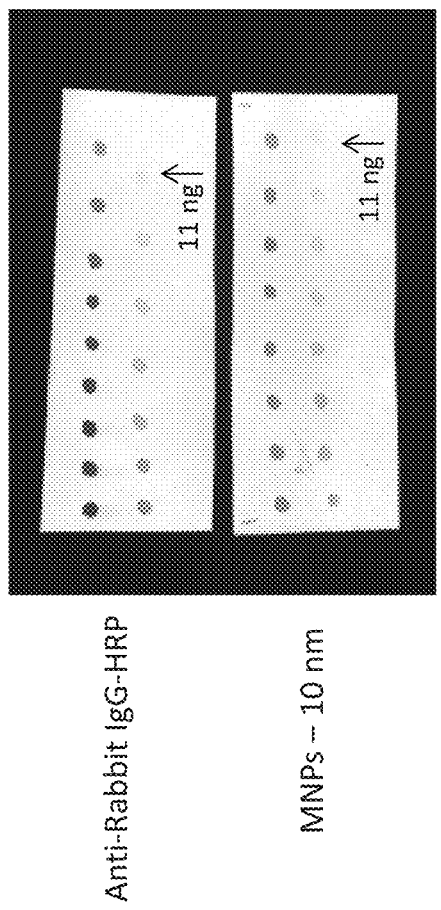
FIG. 8 shows dot blot assays of rabbit IgG with free anti-rabbit IgG-HRP (upper panel) and 10 nm MNPs carrying anti-rabbit IgG-HRP (lower panel) at different target concentrations.

The results are shown in FIG. 8. It can be seen that the results with the 10 nm MNPs are comparable to the results with the free anti-rabbit HRP. For example, the lowest amount of 11 ng Rabbit IgG could be similarly detected by the two methods.

Figure 9:
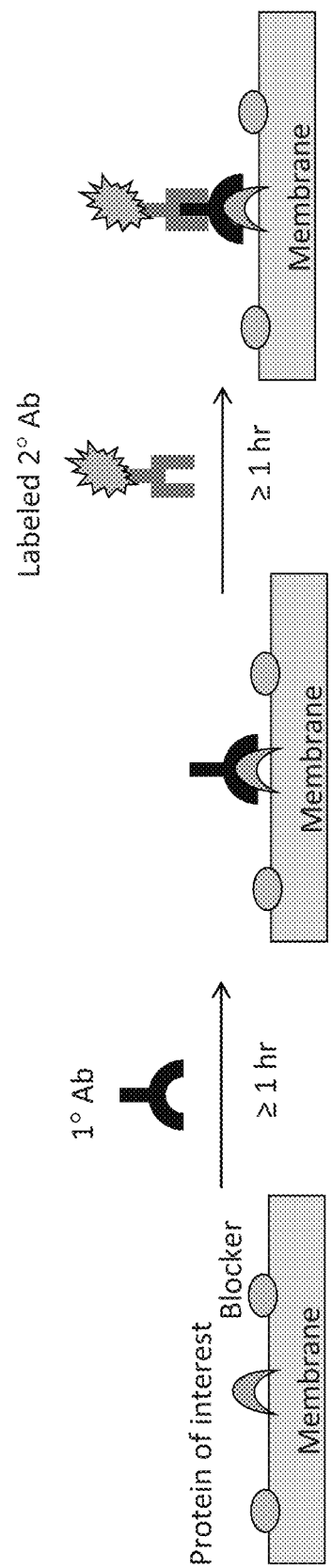
FIG. 9 is a schematic illustration of an assay using free antibody.

Dot Blot Assay with Transferrin/Anti-Transferrin Antibody
Human Transferrin (hT) was spotted on NC membrane, reacted with anti-hT primary antibody and then with 20 nm MNPs (the MNPs that were described in Example 2) (a schematic representation of this procedure is outlined in FIG. 9).

The protocol was composed of the following steps:
1. Dot formation: Four dots of 400 ng human Transferrin (hT, Rockland Immunochemicals) were formed on round (1 inch diameter) nitrocellulose membrane (0.45 μm pore size, Bio-Rad Laboratories). Each dot was formed by placing on the membrane surface a 2 μl drop of hT in PBS buffer at a concentration of 200 μg/ml, and letting it dry at ambient conditions for about 5 minutes.
2. Blocking: The membrane was immersed in Blocking Solution: Nonfat Dry Milk Blocker (Bio-Rad), 10% in TBS buffer with 0.1% Tween 20 (TBST), for 1 h under mild shaking.
3. Binding of primary antibody (1° Ab): The membrane was immersed in Blocking Solution containing 2.1 nM Rabbit anti-hT antibodies (Rockland), for 1 h under mild shaking. The membrane was then washed by immersing in TBST 3 times for 5 min under mild shaking.
4. Binding of Magnetic NanoParticles (MNPs) with labeled secondary antibody (2° Ab): The membrane was immersed in solution of 20 nm iron oxide MNPs with attached Goat anti-Rabbit IgG-HRP (Ocean Nanotech), 0.09 nM in Blocking Solution. The membrane was mildly shaken for 1 hour. Reference reaction (control), in which anti-rabbit HRP was used instead of MNPs, was done under similar conditions (e.g. the same molar concentration and time of reaction). The membrane was then washed by immersing in TBST 3 times for 5 min under mild shaking.
5. Chemiluminescent signal development: About 0.3 ml of Chemiluminescence development solution for HRP (Immun-Star Western Kit, Bio-Rad) was placed on top of the membrane. The signal was recorded after 1 min with exposure time of 6 sec using ChemiDoc MP Imager (Bio-Rad).

Figure 10:
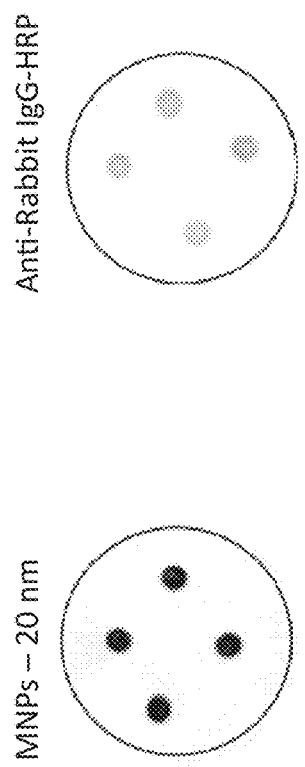
FIG. 10 shows dot blot assays of human Transferrin (hT)/rabbit anti-hT with 20 nm MNPs carrying anti-rabbit IgG-HRP (left panel) and free anti-rabbit IgG-HRP (right panel).

The results are shown in FIG. 10. It was clearly indicated that the signals with the 20 nm MNPs are stronger than the reference signals with the free antibody-HRP. This is probably due to the fact that several antibodies are bound to each MNP (see Example 2).

The main conclusion of this example is that the smaller MNPs (≤30 nm) can function well as efficient capturing and detection agents, and are not limited by their size.

Example 4

Applying Magnetic Field

Figure 11C:
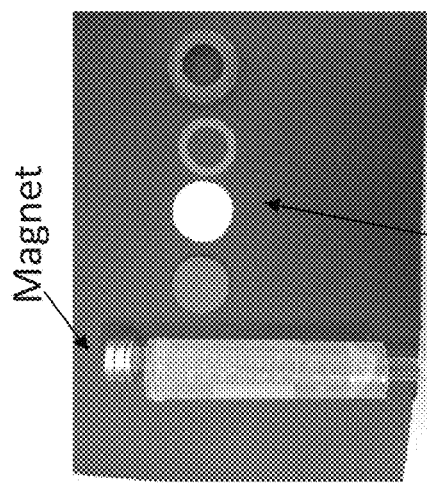
FIG. 11A-C show an exemplary dot blot set up.
Figure 11B:
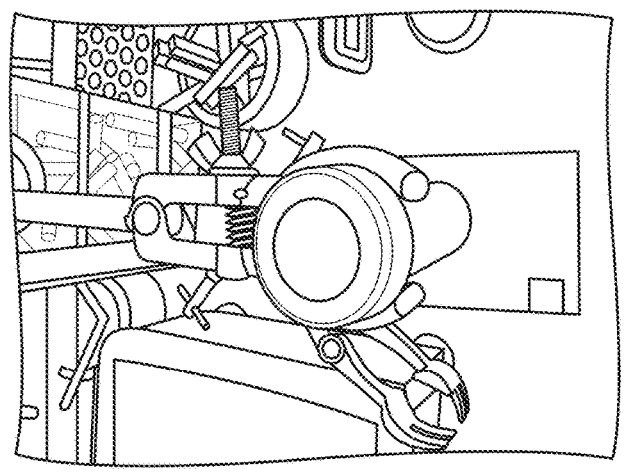
Figure 11A:
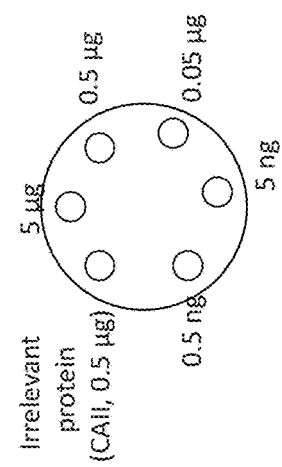

In this Example the effect of applying magnetic field during the assay was tested. Dot blot assays were performed as described above. In this experiment, rabbit IgG, which served as the target protein, was blotted at a series of concentrations (0.5 ng, 5 ng, 0.05 μg, 0.5 μg, and 5 μg) onto a nitrocellulose membrane, and reacted with 0.05 nM MNPs conjugated to anti rabbit IgG-HRP. The detection was performed using chemiluminescence. For applying magnetic field, a neodymium disc magnet (1 inch diameter and thickness, max. surface field 7300 Gauss, K&J Magnetics) was placed under the membrane. A simple magnetic field dot blot device and the experimental settings are presented in FIGS. 11A-C. FIG. 11B is a top view picture of said representative device, and FIG. 11C is a picture of the different elements of the representative device: a neodymium disc magnet, a membrane, and a holder. The experimental setting schematically illustrated in FIG. 11A includes a membrane showing 6 sample zones, five of which are rabbit IgG each at a different concentration and one control sample including a non-relevant antibody (0.5 μg CAII).

Dot blot assays were carried out with and without application of the magnetic field for 5 minutes using four different measuring agents: a complex of 10 nm magnetic nanoparticles-anti-rabbit-HRP antibody, a complex of 20 nm magnetic nanoparticles-anti-rabbit-HRP antibody, a complex of 30 nm magnetic nanoparticles-anti-rabbit-HRP antibody, and free anti-rabbit IgG-HRP (FIG. 12). The results show very weak detection signal of the high rabbit IgG concentrations (5 μg and 0.5 μg) in the dot blot assay with free anti-rabbit IgG and no signal at all in the lower concentrations, with or without applying the magnetic field. The assay using 10 nm magnetic particles-antibody complex without magnetic field showed similar results as the free anti-rabbit IgG-HRP measuring agent, however upon applying magnetic field there is clear improvement of the detection signal and the assay shows sensitivity even to 0.05 μg. The detection signals become even more pronounced when the assays were carried out with 20 nm and 30 nm magnetic particles-antibody complexes and the applied magnetic field. The sensitivity was also improved, showing capabilities to detect lower levels of rabbit IgG even up to 5 ng, even in naked-eye examination. Therefore, the magnetic field clearly improves detection mainly with the 20 nm and 30 nm MNPs.

Example 5

Comparison of a Dot Blot Assay with Separate Antibody Binding Steps and Combined Antibody Binding Steps Dot Blot Assay with Separate Antibody Binding Steps:

In this experiment the nanoparticle complex was associated with a secondary binding agent and applied to the substrate after the substrate was incubated with the first binding agent (a schematic representation of this procedure is outlined in FIG. 13).

The protocol was composed of the following steps (steps 1-3 and 5 are similar to those detailed in Example 3 above):
1. Dot formation: Four dots of 400 ng human Transferrin (hT, Rockland Immunochemicals) were formed on round (1 inch diameter) nitrocellulose membrane (0.45 μm pore size, Bio-Rad Laboratories). Each dot was formed by placing on the membrane surface a 2 μl drop of hT in PBS buffer at a concentration of 200 μg/ml, and letting it dry at ambient conditions for about 5 minutes.
2. Blocking: The membrane was immersed in Blocking Solution: Nonfat Dry Milk Blocker (Bio-Rad), 10% in TBS buffer with 0.1% Tween 20 (TBST), for 1 h under mild shaking.
3. Binding of primary antibody (1° Ab): The membrane was immersed in Blocking Solution containing 2.1 nM Rabbit anti-hT antibodies (Rockland), for 1 h under mild shaking. The membrane was then washed by immersing in TBST 3 times for 5 min under mild shaking.
4. Binding of Magnetic NanoParticles (MNPs) with labeled secondary antibody (2° Ab): The membrane was immersed in solution of 20 nm iron oxide MNPs with attached Goat anti-Rabbit IgG-HRP (Ocean Nanotech), 0.09 nM in Blocking Solution. Magnetic field was applied by placing the membrane on top of a cylindrical neodymium magnet (1 inch diameter and thickness, max. surface field 7300 Gauss, K&J Magnetics). The membrane was mildly shaken for 5 min. For the control experiments, without applying magnetic field, the membrane was mildly shaken for 5 min (Control 1S) or 1 h (Control 1L). The membrane was then washed by immersing in TBST 3 times for 5 min under mild shaking.
5. Chemiluminescent signal development: About 0.3 ml of Chemiluminescence development solution for HRP (Immun-Star Western Kit, Bio-Rad) was placed on top of the membrane. The signal was recorded after 1 min with exposure time of 6 sec using ChemiDoc MP Imager (Bio-Rad).

Dot Blot Assay with Combined Antibody Binding Steps:

In this experiment the nanoparticle complex was associated with a secondary binding agent and pre-incubated with the first binding agent prior to applying the combined solution onto the substrate (a schematic representation of this procedure is outlined in FIG. 14).

Preparation of the Combined Solution:
As a preliminary step, before the assay performance, a combined Solution of a 1° Ab and MNPS labeled with a 2° Ab was prepared. This solution contained Rabbit anti-hT (4.2 nM) and 20 nM MNPs with Goat anti-Rabbit IgG-HRP (0.18 nM) in Blocking Solution, and was equilibrated as ×30 concentrated solution for at least 1 h at room temperature before use.

The steps of Dot formation (1) and Blocking (2) were done as described above.

The Combined Antibody Binding Step:
The membrane was immersed in the Combined Solution. Magnetic field was applied by placing the membrane on top of a cylindrical neodymium magnet (1 inch diameter and thickness, K&J Magnetics). The membrane was mildly shaken for 5 min. For the control experiments, without applying magnetic field, the membrane was mildly shaken for 5 min (Control 2S) or 1 h (Control 2L). The membrane was then washed by immersing in TBST 3 times for 5 min under mild shaking.

The Chemiluminescent signal development step was done as described above.

FIG. 15 summarizes the results of the experiments outlined in Example 5.

The results show the following:

The combined antibody assay with magnetic field for 5 minutes shows a higher detection signal compared to the assay with separate binding steps. Without wishing to be bound by theory this result is probably due to the shortened incubation time in the combined assay which results in less non-specific binding. Furthermore, the combined assay includes less steps of handling, such as washings.

The combined antibody assay with magnetic field for 5 minutes showed a higher signal then that obtained in the combined antibody assay without magnetic field, even when a long (1 hour) binding step is implemented. Comparison of the separate antibody steps assay with the above conditions showed an opposite behavior, i.e., the assay having long (1 hour) binding step without magnetic field shows a higher detection signal than the corresponding assay with applying magnetic field for 5 minutes. In both cases the control experiments, where the assays were without magnetic field for a short period, no detection signal was observed.

At separate binding steps assays the results indicate that the magnetic field accelerates the detection, and exhibits a detection signal after a short period of time, which does not appear so quickly without the employment of magnetic field.

At the combined antibody assays, the binding step is performed in a mixture of free primary antibodies and magnetic nanoparticle-secondary antibody complexes. The procedure may be performed without separating the free primary antibodies from the primary antibodies that are bound to the MNPs, since although both the free primary antibodies and the primary antibodies that are now bound to the magnetic nanoparticles may bind to the target molecule, when applying the magnetic field the magnetic nanoparticles-primary antibodies complexes are drawn to the membrane at an accelerated pace, while the free primary antibodies remain in the medium and bind to the target molecules at a much slower rate. This is a simple competition in which the MNP-bound primary antibodies have a significant advantage. However, without magnetic force, the two primary antibodies (the MNP-bound and the free) compete with one another for binding to the target protein, and therefore the detection signal is lower in this assay after one hour without applying the magnet.

Therefore, the results demonstrate that the assays of the invention provide a significantly shortened assay time with appreciably detectable results.

The different dot blot assay steps and their duration are summarized in Table 1.

| Steps | Standard Dot Blot | Separate Antibodies | Combined Antibodies |
|---|---|---|---|
| Exposure to 1° Ab | 1 hr | 1 hr | None |
| Wash | 15 min | 15 min | None |
| Exposure to 2° Ab | 1 hr | 5 min | 5 min |
| Wash | 15 min | 15 min | 15 min |
| Development and signal detection | 5 min | 5 min | 5 min |
| Total | ~2.5 hr | ~1.5 hr | <0.5 hr |

As can be seen from the table the assay duration is substantially shortened by using the techniques of the invention.

Example 6

Scale-Up of the Magnet Configuration

In Examples 3-5, proof of concept was provided using Dot blot assays. It was then desired to show the applicability of the invention in other assays like Western blot. In such assays the substrate (i.e. membrane) area is larger and thus the magnetic field should be applied uniformly over a larger area.

The first attempts were done using a large block magnet (4 inches×4 inches×1 inch), as shown in FIG. 16. However, the results indicated that the magnetic field over the surface is too weak and non-uniform—stronger near the magnet edges (results not shown). It was previously shown by Urbach et al that the magnetic force which is applied on MNPs is proportional not only to the magnetic field but also to the magnetic field gradient. Therefore, a magnet array was built of small cuboid magnets (¼ inches×¼ inches×½ inch), as shown in FIG. 16. The magnetic polarity is perpendicular (i.e. in Z direction) and opposite for each neighboring magnets ("chessboard configuration"), forming stable structure with high magnetic gradients at the edges of each small magnet as shown by Osman et al.

In order to ensure uniform magnetic force over the whole membrane area, and at the same time provide mixing of the MNPs solution, vertical movement of the membrane in the X and Y directions was enabled. It was done by using a shaker as shown in FIG. 17.

Using this experimental set up yielded good results as described in Examples 7-9 below.

Example 7

Western Blot Assay with Combined Antibody Binding Steps

Assays with Magnetic Acceleration:

Western blot assay was demonstrated with two proteins, human Transferrin (hT, Rockland) and human Serum albumin (hSA, Rockland). The protocol was composed of the following steps:

1. Electrophoresis: Polyacrylamide pre-cast gels (Mini-PROTEAN TGX 4-20% gels, Bio-Rad) were used. Stock solution of both proteins was prepared in standard Laemmli sample buffer with 355 mM 2-mercaptoethanol (Bio-Rad), and pre-treated by heating to 95° C. for 5 min. For each gel, one of the proteins (hT or hSA) was loaded to 9 lanes at a series of amounts (50, 25, 12.5, 6.25, 3.1, 1.6, 0.8. 0.4 and 0.2 ng) in the Laemmli sample buffer with 2-mercaptoethanol. In the $10^{th}$ lane, a molecular weight ladder (Precision Plus Protein Dual Color Standards, Bio-Rad) was loaded. Electrophoretic separation was performed with Mini-PROTEAN Tetra Cell (Bio-Rad), using operation voltage of 180 V for about 40 min.
2. Transfer to membrane: Trans-Blot Turbo transfer system (Bio-Rad) was used to transfer the proteins after electrophoretic separation from the gel to a nitrocellulose membrane that was embedded in Trans-Blot Turbo transfer pack (Bio-Rad).
3. Blocking: The membrane was immersed in Blocking Solution: Nonfat Dry Milk Blocker (Bio-Rad), 10% in TBS buffer with 0.1% Tween 20 (TBST), for 1 h under mild shaking.
4. Preparation of the Combined Solution: As a preliminary step, before the assay performance, a Combined Solution of a 1° Ab and MNPs labeled with a 2° Ab was prepared. This solution contained Rabbit anti-hT or anti-hSA (0.65 nM) and 0.013 nM MNPs with Goat anti-Rabbit IgG-HRP (0.17 nM) in Blocking Solution, and was equilibrated as x30 concentrated solution for at least 1 h at room temperature before use.
5. The combined antibody binding step: The membrane was immersed in the Combined Solution. Magnetic field was applied by placing the membrane on top of a magnet array as described in Example 6 above. The membrane was mildly shaken for 5 min using the shaking device as described in Example 6. The membrane was then washed by immersing in TBST 3 times for 5 min under mild shaking.
6. Chemiluminescent signal development: About 4 ml of Chemiluminescence development solution for HRP (Clarity Western ECL substrate, Bio-Rad) was placed on top of the membrane. The signal was recorded after 5 min using ChemiDoc MP Imager (Bio-Rad).

Reference Assays:

The reference assays were standard Western blot experiments of the same biological models. Steps 1-3 and 6 were done similarly to the assays with magnetic acceleration. Instead of Steps 4 and 5 the following steps were performed:
4. Binding of 1° Ab: The membrane was immersed in 0.65 nM Rabbit anti-hT or anti-hSA antibodies (Rockland) in Blocking Solution for 1 h under mild shaking. The membrane was then washed by immersing in TBST 3 times for 5 min under mild shaking.
5. Binding of labeled 2° Ab: The membrane was immersed in solution of Goat anti-Rabbit IgG-HRP (Jackson), 0.17 nM in Blocking Solution under mild shaking for 1 h. The membrane was then washed by immersing in TBST 3 times for 5 min under mild shaking.

FIGS. 18 and 19 summarize the results of these experiments. The Chemidoc MP images (FIG. 18) and analysis graphs (FIG. 19) reveal higher signals for the short MNP-based assay for both hT and hSA models. More detectable bands were gained for the MNP-based assays, indicating higher assay sensitivity. Without wishing to be bound by theory, the increased signals are probably due to the fact that there are multiple labeled antibodies attached to each MNP (~12 in this case), and thus signal amplification is obtained.

FIG. 18 also shows higher background noise in the MNP-based assays. It was thus required to reduce the background in these assays and gain higher signal:noise ratio (SNR). Many experimental parameters have been tested in order to improve the SNR. The method that yielded the most significant improvement involved drying of the membrane as described in Example 8 below.

Example 8

Signal:Noise Ratio (SNR) Improvement by Membrane Drying

Western blot assays of hT and hSA were performed according to the protocol titled "Assays with magnetic acceleration" in Example 6, with a few changes:
In Step 1 (Electrophoresis), the loaded amounts of the target proteins were: 20, 6.7, 2.2, 0.74, 0.25, 0.082, 0.027 and 0.009 ng.
After Step 2 (Transfer) and before Step 3 (Blocking), the membrane was dried, by placing it in a lab oven at 37° C. under air flow for 30 min. This drying step was applied on one membrane but not on another one which was used as a reference to assess and demonstrate the effect of drying.

FIGS. 20 and 21 summarize the results of these experiments. The Chemidoc MP images (FIG. 20) and analysis graphs (FIG. 21) reveal higher signals and lower background (and thus improved SNR) for the assays that include membrane drying for both hT and hSA models. Without wishing to be bound by theory, the higher signals are probably due to fixation of the target proteins to the membrane, and preventing loss of proteins during the following assay and wash steps; The lower background is probably due to more efficient blocking—the blocking proteins are brought into the membrane by wetting process, which is much faster and efficient than diffusion process as in the standard blocking.

Example 9

ELISA Assay with Combined Antibody Binding Steps

In the following experiments, the goal was to demonstrate that the same principles of using MNPs, as shown in Dot blot and Western blot assays, can be applied in the very commonly used immunoassay method of ELISA.

Assays with Magnetic Acceleration:

ELISA assay was performed with the same two proteins as demonstrated above, hT and hSA. The protocol was composed of the following steps:
  a. Coating the well surface with antigen protein: In a standard 96 well plate (MaxiSorp, Nunc) 100 ul of protein in PBS was placed in each well at a series of concentrations (3.33, 1.11, 0.37, 0.12. 0.04 and 0.01 ng for hT; 1.67, 0.56, 0.19, 0.06 and 0.02 for hSA). These solutions were left in the plate for 2 h at room temperature with mild shaking. Finally, the solutions were removed and the wells were washed 3 times with PBS.
  b. Blocking: To each well, 300 µl Blocking Solution—Nonfat Dry Milk Blocker (Bio-Rad), 2% in PBS buffer—was added, and left for 1 h under mild shaking. This solution was removed from the wells before Step 4.
  c. Preparation of the Combined Solution: As a preliminary step, before the assay performance, a Combined Solution of a 1° Ab and MNPs labeled with a 2° Ab was prepared. This solution contained Rabbit anti-hT or anti-hSA (3.3 nM) and 0.031 nM MNPs with Goat anti-Rabbit IgG-HRP (0.54 nM) in Blocking Solution, and was equilibrated as ×30 concentrated solution for at least 1 h at room temperature before use.
  d. The combined antibody binding step: The Combined Solution was added –100 µl for each well. Magnetic field was applied by placing the plate on top of a magnet array as described in Example 6 above. The plate was mildly shaken for 5 min over the magnet array. Finally, the solution was removed and the wells were washed 3 times with PBS.
  e. Colorimetric signal development: Colorimetric detection solution for HRP (TMB, Dako) was added—100 µl per well. When blue color could be observed in all wells, 50 µl stop solution (2N $H_2SO_4$) was added for each well. The signals at 450 nm were recorded using a plate reader (MultiSkan Go, Thermo).

Reference Assays:

The reference assays were standard ELISA experiments of the same biological models. Steps 1, 2 and 5 were done similarly to the assays with magnetic acceleration. Instead of Steps 3 and 4 the following steps were performed:
3. Binding of 1° Ab: 100 µl of 3.3 nM Rabbit anti-hT or anti-hSA antibodies (Rockland) in Blocking Solution was added for each well and kept for 1 h under mild shaking. Then, the solution was removed and the wells were washed 3 times with PBS.
4. Binding of labeled 2° Ab: 100 µl of 0.54 nM Goat anti-Rabbit IgG-HRP (Jackson) in Blocking Solution was added for each well and kept for 1 h under mild shaking. Then, the solution was removed and the wells were washed 3 times with PBS.

FIG. 22 summarizes the results of these experiments. Higher SNR for the short MNP-based assay for both hT and hSA models was recorded, indicating higher assay sensitivity. This improved SNR originated from both higher signals and lower background (results not shown). Without wishing to be bound by theory, the increased signals are probably due to the fact that there are multiple labeled antibodies attached to each MNP (~17 in this case), and thus signal amplification is obtained.

The invention claimed is:

1. A method for detecting a target molecule in a detection assay, comprising:
   (a) bringing a sample potentially comprising at least one target molecule into contact with a porous substrate, in the absence of magnetic nanoparticle (MNP) complexes, and immobilizing any said target molecule onto the substrate;
   (b) after said step (a), incubating said substrate with magnetic nanoparticle (MNP) complexes while applying a magnetic field using at least one magnet directly under the porous substrate to accelerate the movement of the MNP complexes to the substrate during incubation, said MNP complexes comprising
      (i) MNP having a diameter smaller than 50 nm,
      (ii) a detectable label in addition to said MNP, and
      (iii) a capture molecule being a primary agent that binds to said target molecule, or a secondary agent that binds to said primary agent,
   wherein, when said capture molecule is a secondary agent, the MNP complex is brought into contact with a said primary agent prior to said incubation step or in the course of said incubating step, and
   (c) subjecting the incubated substrate to a detection assay that detects said detectable label and provides a detection signal, wherein the presence of a detection signal is indicative of the presence of the target molecule immobilized on the substrate and attached to the MNP complexes and the intensity of the detection signal is indicative of the amount of the target molecule.

2. The method according to claim 1, wherein said substrate is a porous substrate selected from the group consisting of a membrane, a filter, a gel, and a sponge.

3. The method according to claim 2, wherein the average pore size of the porous substrate is larger than the average diameter of the MNPs.

4. The method according to claim 1, wherein said capture molecule is a primary agent that binds to said target molecule.

5. The method according to claim 1, wherein said capture molecule is a secondary agent that binds to a primary agent that binds to said target molecule.

6. The method according to claim 5, wherein the substrate is incubated with said primary agent prior to said incubation step.

7. The method according to claim 5, wherein the MNP complex comprising said secondary agent is incubated with said primary agent prior to said incubation step.

8. The method according to claim 5, wherein said primary agent is a primary antibody and said secondary agent is a secondary antibody.

9. The method according to claim 1, wherein the detectable label is associated with the MNP in the MNP complex and is selected from the group consisting of a fluorescent compound, a fluorescent particle, an enzyme, a chromophore, an electrochemically active molecule and a radioactive molecule.

10. The method according to claim 1, wherein the detectable label is associated with the capture molecule in the MNP complex and is selected from the group consisting of a fluorescent compound, a fluorescent particle, an enzyme, a chromophore, an electrochemically active molecule and a radioactive molecule.

11. The method according to claim 1, wherein the magnetic field is generated by a magnet array arranged in a chessboard configuration.

12. A method for detecting a target molecule, comprising:
    (a) providing magnetic nanoparticle (MNP) complexes comprising
       (i) a detectable label in addition to said MNP and
       (ii) a secondary binding agent capable of binding a primary binding agent, said primary binding agent being one that binds to said target molecule;
    (b) incubating said MNP complexes with said primary binding agent, thereby forming a second MNP complex comprising MNP, a secondary binding agent, and a primary binding agent;
    (c) bringing a sample potentially comprising at least one said target molecule into contact with a porous substrate in the absence of magnetic nanoparticle (MNP complexes, and immobilizing any said target molecule onto the substrate;
    (d) after said step (c), incubating said substrate with said second MNP complex;
    (e) applying a magnetic field during said step (d) using at least one magnet directly under the porous substrate to accelerate the movement of the second MNP complex to the substrate during incubation; and
    (f) subjecting the incubated substrate that results from step (e) to a detection assay that detects said detectable label and provides a detection signal, wherein the presence of a detection signal is indicative of the presence of the target molecule immobilized on the substrate and attached to the second MNP complex and the intensity of the detection signal is indicative of the amount of the target molecule.

13. The method according to claim 12, wherein said substrate is a porous substrate selected from the group consisting of a membrane, a filter, a gel, and a sponge.

14. The method according to claim 13, wherein the average pore size of the porous substrate is larger than the average diameter of the MNPs.

15. The method according to claim 12, wherein the MNP have a diameter smaller than 50 nm.

16. The method according to claim 12, wherein said primary binding agent is a primary antibody and said secondary binding agent is a secondary antibody.

17. The method according to claim 12, wherein the detectable label is associated with said MNP in the MNP complex.

18. The method according to claim 12, wherein the detectable label is associated with said secondary binding agent in the MNP complex.

19. The method according to claim 1, further comprising a step of drying the substrate and a step of blocking the substrate with a blocking solution prior to said incubation step.

20. The method according to claim 12, further comprising a step of drying the substrate and a step of blocking the substrate with a blocking solution prior to incubating the substrate with said second MNP complex.

21. The method according to claim 1, wherein said detection assay is a dot bolt, slot blot, Western blot, RIA or ELISA assay and said detectable label is one that is detectable in said assay.

22. The method according to claim 12, wherein said detection assay is a dot bolt, slot blot, Western blot, RIA or ELISA assay and said detectable label is one that is detectable in said assay.

23. The method according to claim 22, wherein said detectable label is selected from the group consisting of a fluorescent compound, a fluorescent particle, an enzyme, a chromophore, an electrochemically active molecule and a radioactive molecule.

24. The method according to claim 12, wherein said substrate is selected from the group consisting of a membrane, a filter, a gel and a sponge.

\* \* \* \* \*